(12) United States Patent
Park et al.

(10) Patent No.: US 9,788,846 B2
(45) Date of Patent: Oct. 17, 2017

(54) UNICOMPARTMENTAL CUSTOMIZED ARTHROPLASTY CUTTING JIGS

(71) Applicant: OtisMed Corporation, Alameda, CA (US)

(72) Inventors: Ilwhan Park, Walnut Creek, CA (US); Michael Koehle, San Leandro, CA (US); Lorenzo R. Deveza, San Ramon, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 935 days.

(21) Appl. No.: 14/086,878

(22) Filed: Nov. 21, 2013

(65) Prior Publication Data

US 2014/0128875 A1    May 8, 2014

Related U.S. Application Data

(62) Division of application No. 12/636,939, filed on Dec. 14, 2009, now Pat. No. 8,617,175.
(Continued)

(51) Int. Cl.
*A61B 17/15* (2006.01)
*A61B 17/17* (2006.01)
(Continued)

(52) U.S. Cl.
CPC ........ *A61B 17/1764* (2013.01); *A61B 17/155* (2013.01); *A61B 17/157* (2013.01);
(Continued)

(58) Field of Classification Search
CPC .............. A61B 17/157; A61B 17/1764; A61B 2034/105; A61B 2034/108
See application file for complete search history.

(56) References Cited

U.S. PATENT DOCUMENTS

| 4,517,969 A | 5/1985 | Halcomb et al. |
| 5,035,699 A | 7/1991 | Coates |

(Continued)

FOREIGN PATENT DOCUMENTS

| EP | 0709061 A1 | 5/1996 |
| EP | 1669033 A1 | 6/2006 |

(Continued)

OTHER PUBLICATIONS

Audette et al. "An algorithmic overview of surface registration techniques for medical imaging." Medical Image Analysis, vol. 4, No. 3, Sep. 1, 2000, pp. 201-217.
(Continued)

*Primary Examiner* — Nicholas Woodall
(74) *Attorney, Agent, or Firm* — Polsinelli PC

(57) ABSTRACT

Disclosed herein are unicompartmental femoral and tibial arthroplasty jigs for respectively assisting in the performance of unicompartmental femoral and tibial arthroplasty procedures on femoral and tibial arthroplasty target regions. The jigs each include a mating surface. The mating surface of the femoral jig is configured to matingly receive and contact a generally planar area of an anterior side of a femoral shaft generally proximal of the patellar facet border and generally distal an articularis genu. The mating surface of the tibial jig is configured to matingly receive and contact a generally planar area of an anterior side of a tibial shaft distal of the tibial plateau edge and generally proximal of the tibial tuberosity.

18 Claims, 35 Drawing Sheets

Related U.S. Application Data

(60) Provisional application No. 61/122,842, filed on Dec. 16, 2008.

(51) Int. Cl.
  B33Y 80/00 (2015.01)
  A61B 34/10 (2016.01)
  A61F 2/38 (2006.01)

(52) U.S. Cl.
  CPC ... *A61B 2034/105* (2016.02); *A61B 2034/108* (2016.02); *A61F 2/3836* (2013.01); *B33Y 80/00* (2014.12)

(56) References Cited

U.S. PATENT DOCUMENTS

| | | | |
|---|---|---|---|
| 5,098,436 | A | 3/1992 | Ferrante et al. |
| 5,133,758 | A | 7/1992 | Hollister |
| 5,150,304 | A | 9/1992 | Berchem |
| 5,282,803 | A | 2/1994 | Lackey |
| 5,298,254 | A | 3/1994 | Prewett et al. |
| 5,454,717 | A | 10/1995 | Andreiko |
| 5,514,140 | A | 5/1996 | Lackey |
| 5,735,856 | A | 4/1998 | McCue |
| 5,755,803 | A | 5/1998 | Haines et al. |
| 5,916,221 | A | 6/1999 | Hodorek et al. |
| 6,575,980 | B1 | 6/2003 | Roble et al. |
| 7,203,628 | B1 | 4/2007 | St. Ville |
| 7,373,286 | B2 | 5/2008 | Nikolskiy et al. |
| 7,548,638 | B2 | 6/2009 | Graessner |
| 7,584,080 | B2 | 9/2009 | Taylor et al. |
| 8,115,485 | B1 | 2/2012 | Maier et al. |
| 8,165,657 | B2 | 4/2012 | Krueger |
| D691,719 | S | 10/2013 | Park |
| 8,545,509 | B2 | 10/2013 | Park et al. |
| 8,617,171 | B2 | 12/2013 | Park et al. |
| 8,617,175 | B2 | 12/2013 | Park et al. |
| 8,734,455 | B2 | 5/2014 | Park et al. |
| 8,737,700 | B2 | 5/2014 | Park et al. |
| 8,777,875 | B2 | 7/2014 | Park |
| 8,777,955 | B2 | 7/2014 | Park |
| 9,014,438 | B2 | 4/2015 | Habets |
| 9,265,509 | B2 | 2/2016 | Park et al. |
| 9,451,970 | B2 | 9/2016 | Park |
| 9,549,782 | B2 | 1/2017 | Park et al. |
| 2002/0055679 | A1 | 5/2002 | Sati |
| 2002/0183760 | A1 | 12/2002 | McGovern |
| 2005/0054914 | A1 | 3/2005 | Duerk et al. |
| 2005/0080426 | A1 | 4/2005 | Qian |
| 2005/0149091 | A1 | 7/2005 | Tanamal et al. |
| 2005/0272998 | A1 | 12/2005 | Diehl et al. |
| 2006/0079755 | A1 | 4/2006 | Stazzone et al. |
| 2006/0093240 | A1 | 5/2006 | Sabuncu et al. |
| 2006/0161167 | A1 | 7/2006 | Myers et al. |
| 2006/0244448 | A1 | 11/2006 | Ballon et al. |
| 2007/0010732 | A1 | 1/2007 | DeYoe et al. |
| 2007/0100338 | A1 | 5/2007 | Deffenbaugh et al. |
| 2007/0100462 | A1* | 5/2007 | Lang ............... A61F 2/30942 623/20.29 |
| 2007/0123856 | A1 | 5/2007 | Deffenbaugh et al. |
| 2007/0123857 | A1 | 5/2007 | Deffenbaugh et al. |
| 2007/0173853 | A1 | 7/2007 | MacMillan |
| 2007/0237372 | A1 | 10/2007 | Chen et al. |
| 2007/0270680 | A1 | 11/2007 | Sheffer |
| 2008/0089591 | A1 | 4/2008 | Zhou et al. |
| 2008/0208081 | A1 | 8/2008 | Murphy |
| 2009/0085567 | A1 | 4/2009 | Kimmlingen et al. |
| 2009/0089026 | A1 | 4/2009 | Rodriguez Y Baena |
| 2009/0125114 | A1 | 5/2009 | May et al. |
| 2009/0264894 | A1 | 10/2009 | Wasielewski |
| 2009/0285465 | A1 | 11/2009 | Haimerl et al. |
| 2010/0016986 | A1 | 1/2010 | Trabish |
| 2010/0023015 | A1* | 1/2010 | Park ............... A61B 17/15 606/87 |
| 2010/0036252 | A1 | 2/2010 | Chalana et al. |
| 2010/0274253 | A1 | 10/2010 | Ure |
| 2011/0009868 | A1 | 1/2011 | Sato |
| 2013/0190767 | A1 | 7/2013 | Park et al. |
| 2014/0078139 | A1 | 3/2014 | Park et al. |
| 2014/0081277 | A1 | 3/2014 | Park et al. |
| 2016/0015466 | A1 | 1/2016 | Park et al. |
| 2016/0095609 | A1 | 4/2016 | Park et al. |
| 2016/0213491 | A1 | 7/2016 | Schoenefeld |
| 2016/0228194 | A1 | 8/2016 | Park et al. |
| 2016/0228195 | A1 | 8/2016 | Park et al. |
| 2016/0228196 | A1 | 8/2016 | Park et al. |
| 2016/0228197 | A1 | 8/2016 | Park et al. |
| 2016/0270857 | A1 | 9/2016 | Park et al. |
| 2016/0270858 | A1 | 9/2016 | Park et al. |
| 2016/0270859 | A1 | 9/2016 | Park et al. |
| 2016/0310217 | A1 | 10/2016 | Park et al. |
| 2016/0354092 | A1 | 12/2016 | Park |
| 2017/0007275 | A1 | 1/2017 | Park et al. |

FOREIGN PATENT DOCUMENTS

| | | |
|---|---|---|
| FR | 2478462 A1 | 9/1981 |
| GB | 2447702 A | 9/2008 |
| JP | 10-94538 | 4/1998 |
| JP | 2001-092950 | 4/2001 |
| JP | P 2005-287813 | 10/2005 |
| WO | WO 98/32384 | 7/1998 |
| WO | WO 00/35346 | 6/2000 |
| WO | WO 2006/127486 A2 | 11/2006 |
| WO | WO 2007/097853 A2 | 8/2007 |
| WO | WO 2007/097854 A2 | 8/2007 |
| WO | WO 2007/137327 A1 | 12/2007 |
| WO | WO 2008/014618 A1 | 2/2008 |
| WO | WO 2008/091358 A1 | 7/2008 |
| WO | WO 2009/134620 A2 | 11/2009 |

OTHER PUBLICATIONS

European Search Report, EP09739422.5, dated Mar. 28, 2013, 9 pages.
Final Office Action, U.S. Appl. No. 12/546,545, dated Oct. 7, 2013, 24 pages.
Final Office Action, U.S. Appl. No. 12/390,667, dated Oct. 25, 2013, 17 pages.
Ibáñez et al., The ITK Software Guide, Second Edition, Updated for ITK version 2.4, Nov. 21, 2005, pp. 114, 396-411, and 426.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/946,002, dated Oct. 2, 2013, 39 pages.
Non-Final Office Action, U.S. Appl. No. 13/723,904, mailed Aug. 9, 2013, 6 pages.
Non-Final Office Action, U.S. Appl. No. 13/730,608, dated Oct. 7, 2013, 10 pages.
Notice of Allowance, U.S. Appl. No. 13/086,275, mailed Aug. 27, 2013, 31 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Xie et al. "Segmentation by surface-to-image registration." proceedings of SPIE, vol. 6144, Mar. 2, 2006, pp. 614405-1-614405-7.

(56) References Cited

OTHER PUBLICATIONS

European Search Report, EP 09835583.7, dated May 9, 2014.
European search Report, European Appl. No. 08863202.1, dated May 16, 2014.
Extended European search Report, European Appl. No. 13188389. 4, dated Jan. 8, 2014.
Final Office Action, U.S. Appl. No. 11/641,569, dated Nov. 29, 2013, 20 pages.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 12/505,056, dated Dec. 30, 2013, 48 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Japanese Office Action, JP Application No. 2011-507530, dated Dec. 17, 2013, 8 pages.
Non-Final Office Action, U.S. Appl. No. 11/946,002, dated Feb. 6, 2014, 46 pages.
Non-Final Office Action, U.S. Appl. No. 13/488,505, dated Jul. 17, 2014.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/760,388, dated Jan. 22, 2014, 13 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014
Preliminary Amendment, U.S. Appl. No. 13/731,850, filed Apr. 11, 2014, 8 pages.
Response to Final Office Action, U.S. Appl. No. 11/641,569, dated Jan. 29, 2014, 10 pages.
Response to Final Office Action, U.S. Appl. No. 11/642,385, dated Jul. 22, 2014.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Restriction, U.S. Appl. No. 13/488,505, dated May 5, 2014, 7 pages.
Restriction Requirement, U.S. Appl. No. 13/488,505, dated Mar. 4, 2014, 5 pages.
Siemens Magnetom Sonata 1.5T Technical Specifications, pp. 1-4, accessed online Jan. 28, 2014.
Supplementary European Search Report and Opinion, EP 09739474.6, dated Feb. 27, 2014, 7 pages.
U.S. Appl. No. 14/272,147, filed May 7, 2014, Park et al.
U.S. Appl. No. 14/335,431, filed Jul. 18, 2014, Park et al.
U.S. Appl. No. 14/335,460, filed Jul. 18, 2014, Park et al.
U.S. Appl. No. 13/960,498, filed Aug. 6, 2013, Song.
U.S. Appl. No. 14/011,998, filed Aug. 28, 2013, Park et al.
Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
Calvo et al., "High Resolution MRI Detects Cartilage Swelling at the Early Stages of Experimental Osteoarthritis," OARSI, 2001, pp. 463-472.
Delp et al. "An Interactive Graphics-Based Model of the lower Extremity to Study Orthopaedic Surgical Procedures." *IEEE Transactions on Biomedical Engineering*, vol. 37, No. 8, Aug. 1990.
Garg, A. et al.. "Prediction of Total Knee Motion Using a Three-Dimensional Computer-Graphics Model." *J. Biomechanics*, vol. 23, No. 1, pp. 45-58, 1990.
Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.
Taylor et al., "Computer-integrated revision total hip replacement surgery: concept and preliminary results," Medical Image Analysis (1999) vol. 3, No. 3, pp. 301-319.
Walker, P. S. et al. "Range of Motion in Total Knee Arthroplasty: A Computer Analysis." *Clinical Orthopaedics and Related Research*, No. 262, Jan. 1991.
Advisory Action, U.S. Appl. No. 11/642,385, dated Aug. 1, 2014.
Amendment and Response After Final Office Action, U.S. Appl. No. 11/656,323, dated Aug. 25, 2014.
Amendment Under 37 CFR 1.312, U.S. Appl. No. 14/824,731, dated Dec. 28, 2015.
Appeal Brief, U.S. Appl. No. 11/642,385, dated Oct. 7, 2014.
Appeal Brief, U.S. Appl. No. 11/946,002, dated Oct. 13, 2016.
Australian Patent Examination Report No. 1, AU 2013200861, dated Mar. 3, 2015.
Canadian Office Action, CA2721735, dated Aug. 24, 2016.
Canadian Office Action, CA2642616, dated Apr. 22, 2015.
Canadian Office Action, CA2708393, dated Jul. 29, 2014.
Canadian Office Action, CA2642616, dated Feb. 26, 2016.
Canadian Office Action, CA2708393, dated Mar. 11, 2016.
Canadian Office Action, CA2708393, dated May 7, 2015.
Canadian Office Action, CA2721735, dated Jul. 7, 2015.
Canadian Office Action, CA2721762, dated Nov. 10, 2015.
Canadian Office Action, CA2721762, dated Jul. 20, 2016.
Decision on Appeal, U.S. Appl. No. 12/391,008, dated Dec. 11, 2015.
Decision on Appeal, U.S. Appl. No. 11/642,385, dated Mar. 2, 2017.
EP Communication pursuant to Article 94(3) EPC, EP10192631.9, dated Feb. 12, 2016.
EP Search Report and Opinion, EP09800841.0, dated Mar. 22, 2016.
EP Examination Report, EP13188389.4, dated Jan. 30, 2017.
EP Examination Report, EP09739422.5, dated Mar. 7, 2017.
European Examination Report, EP10192631.9, dated Feb. 11, 2015.
European Patent Office, Summons to Attend Oral Proceedings, EP07749030.8, dated Sep. 10, 2015.
European Search Report, EP09718014.5, dated May 13, 2015.
European Search Report, EP09718041.8, dated May 12, 2015.
European Search Report, EP09823986.6, dated Sep. 23, 2014.
Examiner's Answer in appeal, U.S. Appl. No. 11/946,002, dated Jan. 23, 2017.

(56) References Cited

OTHER PUBLICATIONS

Extended European Search Report, EP11769533.8, dated Jan. 9, 2017.
Extended European Search Report, EP14765072.5, dated Sep. 22, 2016.
Final Office Action, U.S. Appl. No. 11/946,002, dated Sep. 17, 2014.
Final Office Action, U.S. Appl. No. 11/946,002, dated Nov. 30, 2015.
Final Office Action, U.S. Appl. No. 13/923,093, dated Jul. 14, 2016.
Final Office Action, U.S. Appl. No. 14/011,998, dated Jul. 14, 2016.
Final Office Action, U.S. Appl. No. 14/084,255, dated Jul. 26, 2016.
Final Office Action, U.S. Appl. No. 14/869,762, dated Oct. 6, 2016.
Final Rejection, U.S. Appl. No. 13/749,095, dated Dec. 24, 2015.
Final Rejection, U.S. Appl. No. 14/476,500, dated Feb. 1, 2016.
International Search Report and Written Opinion, PCT/US2014/030496, dated Aug. 6, 2014.
International Search Report and Written Opinion, PCT/US2016/034847, dated Dec. 8, 2016.
Japanese Office Action, JP2014-147908, dated Jun. 9, 2015.
Non-Final Office Action, U.S. Appl. No. 14/335,460, dated Aug. 30, 2016.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 11/656,323, dated Sep. 18, 2014.
Non-Final Office Action, U.S. Appl. No. 11/946,002, dated May 18, 2016.
Non-Final Office Action, U.S. Appl. No. 11/946,002, dated Jun. 29, 2015.
Non-Final Office Action, U.S. Appl. No. 13/749,095, dated Sep. 10, 2015.
Non-Final Office Action, U.S. Appl. No. 13/923,093, dated Dec. 2, 2015.
Non-Final Office Action, U.S. Appl. No. 13/960,498, dated Feb. 9, 2016.
Non-Final Office Action, U.S. Appl. No. 14/011,998, dated Feb. 12, 2016.
Non-Final Office Action, U.S. Appl. No. 14/084,255, dated Jan. 19, 2017.
Non-Final Office Action, U.S. Appl. No. 14/084,255, dated Feb. 25, 2016.
Non-Final Office Action, U.S. Appl. No. 14/086,849, dated Nov. 2, 2016.
Non-Final Office Action, U.S. Appl. No. 14/272,147, dated Jun. 17, 2016.
Non-Final Office Action, U.S. Appl. No. 14/335,431, dated Sep. 14, 2016.
Non-Final Office Action, U.S. Appl. No. 14/476,500, dated Jun. 18, 2015.
Non-Final Office Action, U.S. Appl. No. 14/869,762, dated Mar. 31, 2016.
Non-Final Office Action, U.S. Appl. No. 14/928,767, dated Jan. 12, 2017.
Non-Final Office Action, U.S. Appl. No. 14/946,106, dated Jun. 23, 2016.
Non-Final Office Action, U.S. Appl. No. 15/168,359, dated Dec. 30, 2016.
Non-Final Office Action, U.S. Appl. No. 15/168,359, dated Aug. 17, 2016.
Non-Final Office Action, U.S. Appl. No. 15/168,405, dated Jan. 12, 2017.
Non-Final Office Action, U.S. Appl. No. 15/168,405, dated Aug. 3, 2016.
Notice of Allowance, U.S. Appl. No. 11/656,323, dated Feb. 3, 2015.
Notice of Allowance, U.S. Appl. No. 12/391,008, dated Dec. 22, 2015.
Notice of Allowance, U.S. Appl. No. 13/731,697, dated Jul. 29, 2015.
Notice of Allowance, U.S. Appl. No. 13/749,095, dated Apr. 7, 2016.
Notice of Allowance, U.S. Appl. No. 13/923,093, dated Jan. 4, 2017.
Notice of Allowance, U.S. Appl. No. 14/011,998, dated Jan. 11, 2017.
Notice of Allowance, U.S. Appl. No. 14/272,147, dated Nov. 21, 2016.
Notice of Allowance, U.S. Appl. No. 14/335,460, dated Mar. 27, 2017.
Notice of Allowance, U.S. Appl. No. 14/476,500, dated May 19, 2016.
Notice of Allowance, U.S. Appl. No. 14/824,731, dated Oct. 20, 2015.
Notice of Allowance, U.S. Appl. No. 14/946,106, dated Feb. 3, 2017.
Notice of Allowance, U.S. Appl. No. 15/167,614, dated Aug. 26, 2016.
Notice of Allowance, U.S. Appl. No. 15/242,312, dated Jan. 3, 2017.
Preliminary Amendment, U.S. Appl. No. 15/202,417, dated Sep. 15, 2016.
Reply Brief, U.S. Appl. No. 11/642,385, dated Jan. 23, 2015.
Response to Final Office Action, U.S. Appl. No. 11/946,002, dated Mar. 29, 2016.
Response to Final Office Action, U.S. Appl. No. 13/749,095, dated Feb. 17, 2016.
Response to Final Office Action, U.S. Appl. No. 14/084,255, dated Dec. 22, 2016.
Response to Final Office Action, U.S. Appl. No. 14/869,762, dated Jan. 4, 2017.
Response to Non-Final Office Action, U.S. Appl. No. 13/731,697, dated May 26, 2015.
Response to Non-Final Office Action, U.S. Appl. No. 13/749,095, dated Apr. 20, 2015.
Response to Non-Final Office Action, U.S. Appl. No. 11/946,002, dated Sep. 29, 2015.
Response to Non-Final Office Action, U.S. Appl. No. 13/923,093, dated May 2, 2016.
Response to Non-Final Office Action, U.S. Appl. No. 14/011,998, dated May 6, 2016.
Response to Non-Final Office Action, U.S. Appl. No. 14/084,255, dated May 23, 2016.
Response to Non-Final Office Action, U.S. Appl. No. 14/272,147, dated Sep. 13, 2016.
Response to Non-Final Office Action, U.S. Appl. No. 14/335,460, dated Jan. 27, 2017.
Response to Non-Final Office Action, U.S. Appl. No. 14/476,500, dated Oct. 16, 2015.
Response to Non-Final Office Action, U.S. Appl. No. 14/869,762, dated Jun. 29, 2016.
Response to Non-Final Office Action, U.S. Appl. No. 15/168,359, dated Oct. 24, 2016.
Response to Non-Final Office Action, U.S. Appl. No. 15/168,405 dated Oct. 31, 2016.
Response to Non-Final Office Action, U.S. Appl. No. 15/168,359, dated Mar. 31, 2017.
Response to Non-Final Office Action, U.S. Appl. No. 14/086,849, dated Apr. 3, 2017.
Response to Restriction, U.S. Appl. No. 14/476,500, dated Mar. 17, 2015.
Response to Restriction, U.S. Appl. No. 13/749,095, dated Nov. 13, 2014.
Response to Restriction, U.S. Appl. No. 13/960,498, dated Nov. 19, 2015.
Response to Restriction, U.S. Appl. No. 14/335,431, dated Aug. 31, 2016.
Response to Restriction, U.S. Appl. No. 15/274,717, dated Jan. 9, 2017.
Restriction Requirement, U.S. Appl. No. 14/476,500, dated Feb. 25, 2015.
Restriction Requirement, U.S. Appl. No. 13/749,095, dated Sep. 25, 2014.

(56) References Cited

OTHER PUBLICATIONS

Restriction Requirement, U.S. Appl. No. 13/960,498, dated Sep. 23, 2015.
Restriction Requirement, U.S. Appl. No. 14/335,431, dated Aug. 12, 2016.
Restriction Requirement, U.S. Appl. No. 15/274,717, dated Nov. 16, 2016.
Supplemental Amendment, U.S. Appl. No. 14/869,762, dated Jan. 13, 2017.

* cited by examiner

FROM [BLOCK 120] IN FIG.1C-1

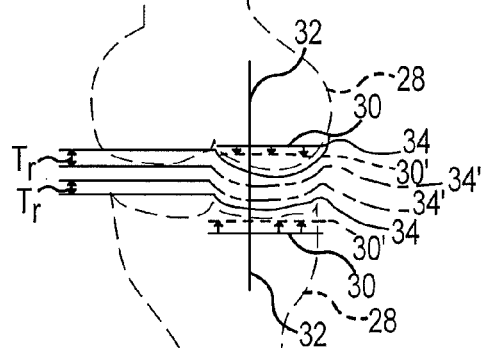

DETERMINE CORRECT ADJUSTMENT VALUE $T_r$, FOR 3D ARTHROPLASTY UNICOMPARTMENTAL IMPLANT MODEL 34 FOR FURTHER ADJUSTMENT (34') OF SHAPE MATCHING TO RESTORE PATIENT'S JOINT LINE TO ITS PRE-DEGENERATIVE STATE BY MEASURING THE MINIMUM CARTILAGE THICKNESS FOR THE UNDAMAGED FEMORAL CONDYLE AND UNDAMAGED PORTION OF THE TIBIA AND USING THE MEASUREMENT AS THE CARTILAGE THICKNESS REFERENCE FOR POP [BLOCK 123]

CONTINUED IN [BLOCK 125] IN FIG.1E

FIG.1C-2

UNICOMPARTMENTAL CUSTOMIZED ARTHROPLASTY CUTTING JIGS

CROSS REFERENCE TO RELATED APPLICATIONS

The present application is a divisional of U.S. application Ser. No. 12/636,939, filed Dec. 14, 2009, which application claims priority under 35 U.S.C. §119 to U.S. provisional patent application 61/122,842, which was filed Dec. 16, 2008, entitled "Uni-Compartmental Customized Arthroplasty Cutting Jigs And Methods Of Making The Same." All of the above-identified applications are hereby incorporated by reference in their entirety into the present application.

FIELD OF THE INVENTION

The present invention relates to arthroplasty cutting jigs and systems and methods for manufacturing such jigs. More specifically, the present invention relates to uni-compartmental customized arthroplasty cutting jigs and automated systems and methods of manufacturing such jigs.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. Typically, a candidate for a TKA has significant wear or damage in two or more "compartments" of the knee. The knee is generally divided into three "compartments": medial (the inside part of the knee), lateral (the outside part of the knee) and the patellofemoral (the joint between the kneecap and the thighbone). During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Another type of procedure is a unicompartmental (knee) arthroplasty or partial knee replacement ("UKA") in which only a portion (or a single compartment) of the knee is replaced with prosthetic implants. Typically, a candidate for a UKA has significant wear or damage confined to primarily one compartment of the knee. A UKA may be a less invasive approach than a TKR and may have a quicker recovery time. A UKA may be utilized to prevent the spread of disease, such as in the early stages of osteoarthritis, where the disease has only affected a portion of the knee and it is desirable to prevent the disease from spreading to other portions of the knee.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA or a UKA procedure. A one- to two-millimeter translational misalignment, or a one- to two-degree rotational misalignment, may result in imbalanced ligaments, and may thereby significantly affect the outcome of the procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument. However, under some methods, it may be difficult to determine the proper orientation of an arthroplasty jig, and more specifically, of a unicompartmental arthroplasty jig.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone models on the computer screen is inefficient and unnecessarily raises the time, manpower and costs associated with producing the customized arthroplasty jigs. Furthermore, a less manual approach may improve the accuracy of the resulting jigs.

There is a need in the art for customized uni-compartmental arthroplasty jigs and methods of planning and generating such a jig. There is a need in the art for a system and method for reducing the labor associated with generating customized arthroplasty jigs. There is also a need in the art for a system and method for increasing the accuracy of customized arthroplasty jigs.

SUMMARY

Disclosed herein is an unicompartmental femoral arthroplasty jig for assisting in the performance of an unicompartmental femoral arthroplasty procedure on a femoral arthroplasty target region. In one embodiment, the unicompartmental femoral arthroplasty jig includes a first side, a second side and a mating surface. The second side is generally opposite the first side. The mating surface is in the first side and configured to matingly receive and contact certain surfaces of the femoral arthroplasty target region. The certain surfaces are limited to and include a medial articular condyle surface, an articular trochlear groove surface, and a generally planar area of an anterior side of a femoral shaft. The first side is configured to be oriented towards the femoral arthroplasty target region surface when the mating surface matingly receives and contacts the certain surfaces.

In one version of the embodiment, the unicompartmental femoral arthroplasty jig further includes a cutting guide surface positioned and oriented relative to the mating surface to result in a cut in the femoral arthroplasty target region with a desired position and orientation. In some cases, the desired position and orientation may allow a prosthetic femoral implant to restore a patient's knee joint to a natural alignment and, in other cases, the restoration may be to a zero degree mechanical axis alignment.

In one version of the embodiment of the unicompartmental femoral arthroplasty jig, the certain surfaces associated with the medial articular condyle surface are generally limited to an anterior and distal regions of the medial articular condyle surface.

In one version of the embodiment of the unicompartmental femoral arthroplasty jig, the certain surfaces associated with the articular trochlear groove surface are generally limited to an anterior and distal regions of a medial articular trochlear groove surface.

In one version of the embodiment of the unicompartmental femoral arthroplasty jig, the certain surfaces associated with the articular trochlear groove surface are generally limited to regions of a lateral articular trochlear groove surface and a medial articular trochlear groove surface.

In one version of the embodiment of the unicompartmental femoral arthroplasty jig, the certain surfaces associated with the articular trochlear groove surface are generally limited to anterior and distal regions of a lateral articular trochlear groove surface and anterior and distal regions of a medial articular trochlear groove surface.

In one version of the embodiment of the unicompartmental femoral arthroplasty jig, the certain surfaces associated with the generally planar area of the anterior side of the femoral shaft are generally limited to being generally distal of the articulars genu and generally proximal of the anterior patellar facet boarder.

In one version of the embodiment of the unicompartmental femoral arthroplasty jig, the certain surfaces associated with the generally planar area of the anterior side of the femoral shaft are generally limited to: being generally distal of the articulars genu and generally proximal of the anterior patellar facet boarder; and at least one contact point with the anterior patellar facet boarder.

Also disclosed herein is an unicompartmental tibial arthroplasty jig for assisting in the performance of an unicompartmental tibial arthroplasty procedure on a tibial arthroplasty target region. In one embodiment, the unicompartmental tibial arthroplasty jig includes a first side, a second side and a mating surface. The second side is generally opposite the first side. The mating surface is in the first side and configured to matingly receive and contact certain surfaces of the tibial arthroplasty target region. The certain surfaces are limited to and include a medial articular plateau surface, an intercondyloid eminence surface, and a generally planar area of an anterior side of a tibial shaft. The first side is configured to be oriented towards the tibial arthroplasty target region surface when the mating surface matingly receives and contacts the certain surfaces.

In one version of the embodiment, the unicompartmental tibial arthroplasty jig further includes a cutting guide surface positioned and oriented relative to the mating surface to result in a cut in the tibial arthroplasty target region with a desired position and orientation. In some cases, the desired position and orientation may allow a prosthetic tibial implant to restore a patient's knee joint to a natural alignment and, in other cases, the restoration may be to a zero degree mechanical axis alignment.

In one version of the embodiment of the unicompartmental tibial arthroplasty jig, the certain surfaces associated with the generally planar area of the anterior side of the tibial shaft are generally limited to being generally distal of the tibial plateau edge and generally proximal of the tibial tuberosity.

In one version of the embodiment of the unicompartmental tibial arthroplasty jig, the certain surfaces associated with the intercondyloid eminence are generally limited to a medial upslope of the intercondyloid eminence.

In one version of the embodiment of the unicompartmental tibial arthroplasty jig, the certain surfaces associated with the intercondyloid eminence are generally limited to a medial upslope of the intercondyloid eminence and a region extending from anterior the intercondyloid eminence to towards a tuberosity over an edge transition from a tibial plateau region. In some such cases, at least one of the certain surfaces associated with the intercondyloid eminence merges with at least one of the certain surfaces associated with the generally planar area of the anterior side of the tibial shaft.

Further disclosed herein is an unicompartmental femoral arthroplasty jig for assisting in the performance of an unicompartmental femoral arthroplasty procedure on a femoral arthroplasty target region. In one embodiment, the unicompartmental femoral arthroplasty jig includes a first side, a second side and a mating surface. The second side is generally opposite the first side. The mating surface is in the first side and configured to matingly receive and contact a generally planar area of an anterior side of a femoral shaft generally proximal of the patellar facet boarder and generally distal an articularis genu. The first side is configured to be oriented towards the femoral arthroplasty target region surface when the mating surface matingly receives and contacts the planar area.

Yet further disclosed herein is an unicompartmental tibial arthroplasty jig for assisting in the performance of an unicompartmental tibial arthroplasty procedure on a tibial arthroplasty target region. In one embodiment, the unicompartmental tibial arthroplasty jig includes a first side, a second side and a mating surface. The second side is generally opposite the first side. The mating surface is in the first side and configured to matingly receive and contact a generally planar area of an anterior side of a tibial shaft distal of the tibial plateau edge and generally proximal of the tibial tuberosity. The first side is configured to be oriented towards the tibial arthroplasty target region surface when the mating surface matingly receives and contacts the planar area.

In one version of the embodiment of the unicompartmental tibial arthroplasty jig, the generally planar area includes a portion that extends distally from generally the tibial plateau edge to a point generally even with the beginning of a distal half to distal third of the tibial tuberosity. In some such cases, the portion extends medial-lateral from a medial edge of a medial tibia condyle to a point generally even with a medial edge of the tibial tuberosity.

In one version of the embodiment of the unicompartmental tibial arthroplasty jig, the generally planar area includes a portion that extends distally from generally the tibial plateau edge to a point near a proximal boundary of the tibial tuberosity. In some such cases, the portion extends medial-lateral generally between a lateral edge and a medial edge of the tibial tuberosity.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Disclosed herein are customized uni-compartmental arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

Figure 1A:
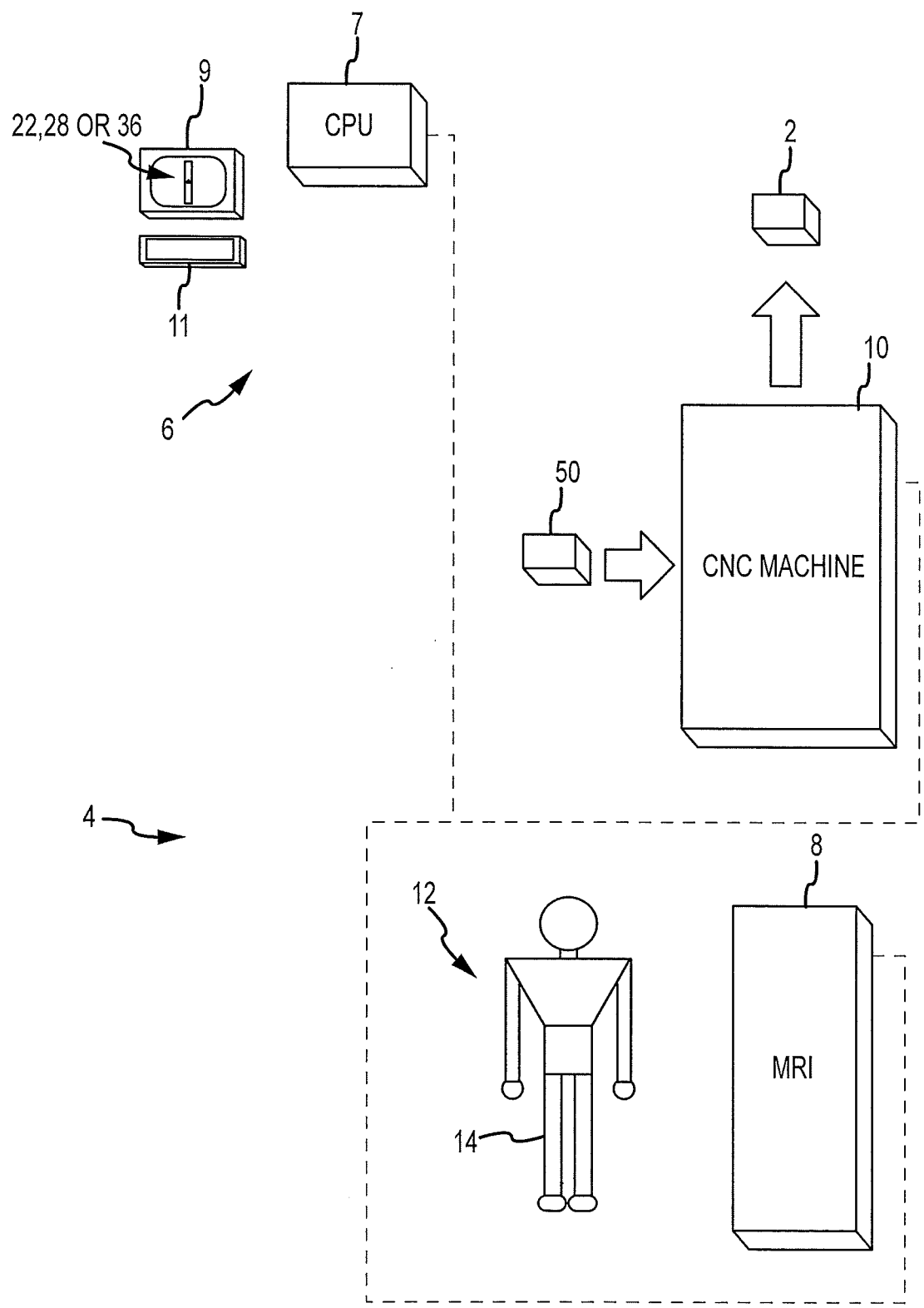
FIG. 1A is a schematic diagram of a system for employing the automated jig production method disclosed herein.

A. Overview of System and Method for Manufacturing Customized Arthroplasty Cutting Jigs For an overview discussion of the systems 4 for, and methods of, producing the customized uni-compartmental arthroplasty jigs 2, reference is made to FIGS. 1A-1L. FIG. 1A is a schematic diagram of a system 4 for employing the automated jig production method disclosed herein. FIGS. 1B-1E are flow chart diagrams outlining the jig production method disclosed herein. FIGS. 1F-1L show the 3D computer models of several steps outlined in the flow chart diagrams of FIGS. 1B-1E. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. The resulting "saw cut and drill hole data" 44 is referenced to the restored bone models 28 to provide saw cuts and drill holes that will allow arthroplasty implants to restore the patient's joint to its pre-degenerated or natural alignment state. Depending on the damage to the actual cartilage and bone of the patient's joint that is the target of the arthroplasty, the bone model 22 may or may not be "restored" to a greater or lesser extent into a restored bone model 28.

The second section, which is discussed with respect to FIG. 1A and [blocks 100-105 and 130-145] of FIGS. 1B-1E, pertains to an example method of importing into 3D computer generated uni-compartmental jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
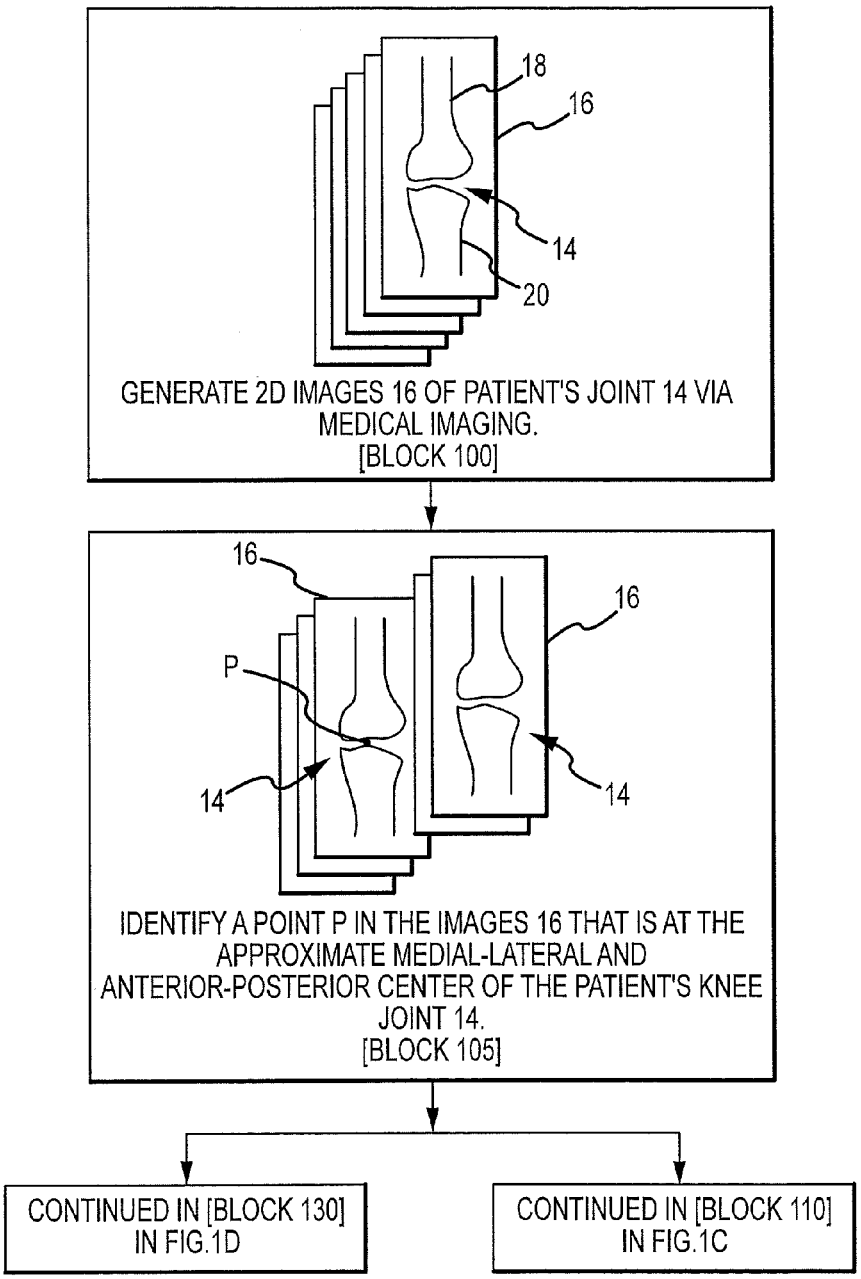
FIGS. 1B-1E are flow chart diagrams outlining the jig production method disclosed herein.
Figures 1, 1C:
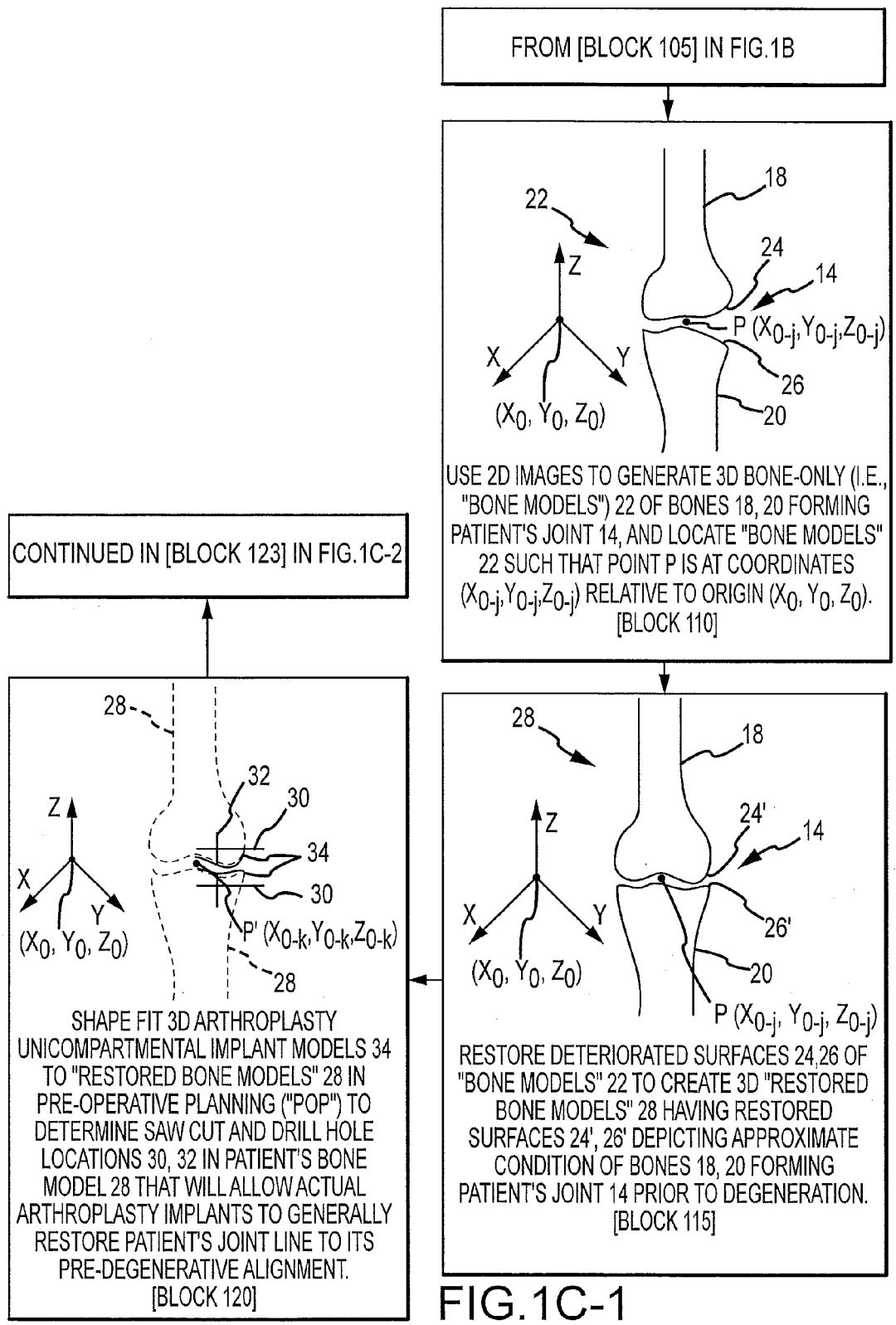
Figure 1D:
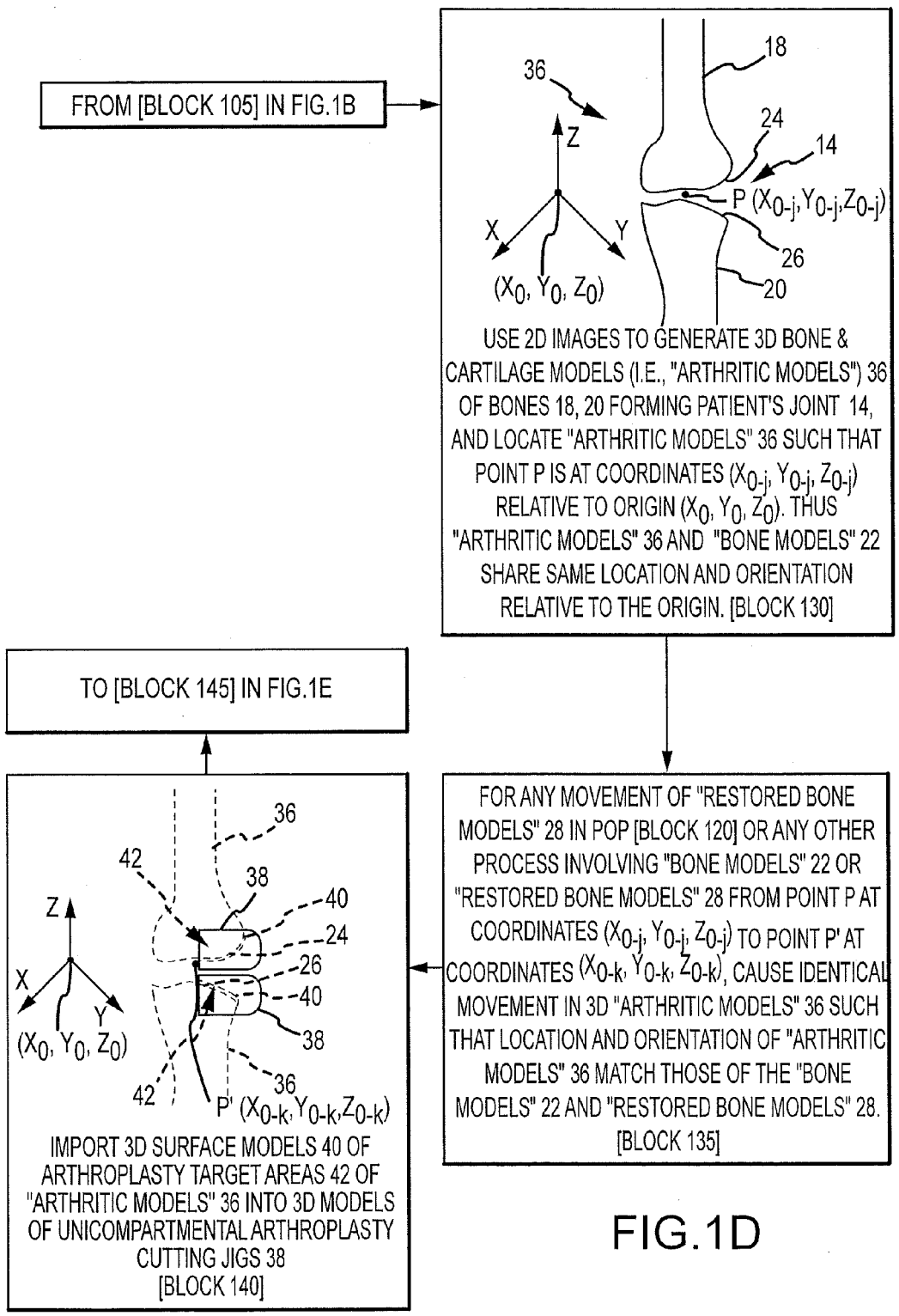
Figure 1E:
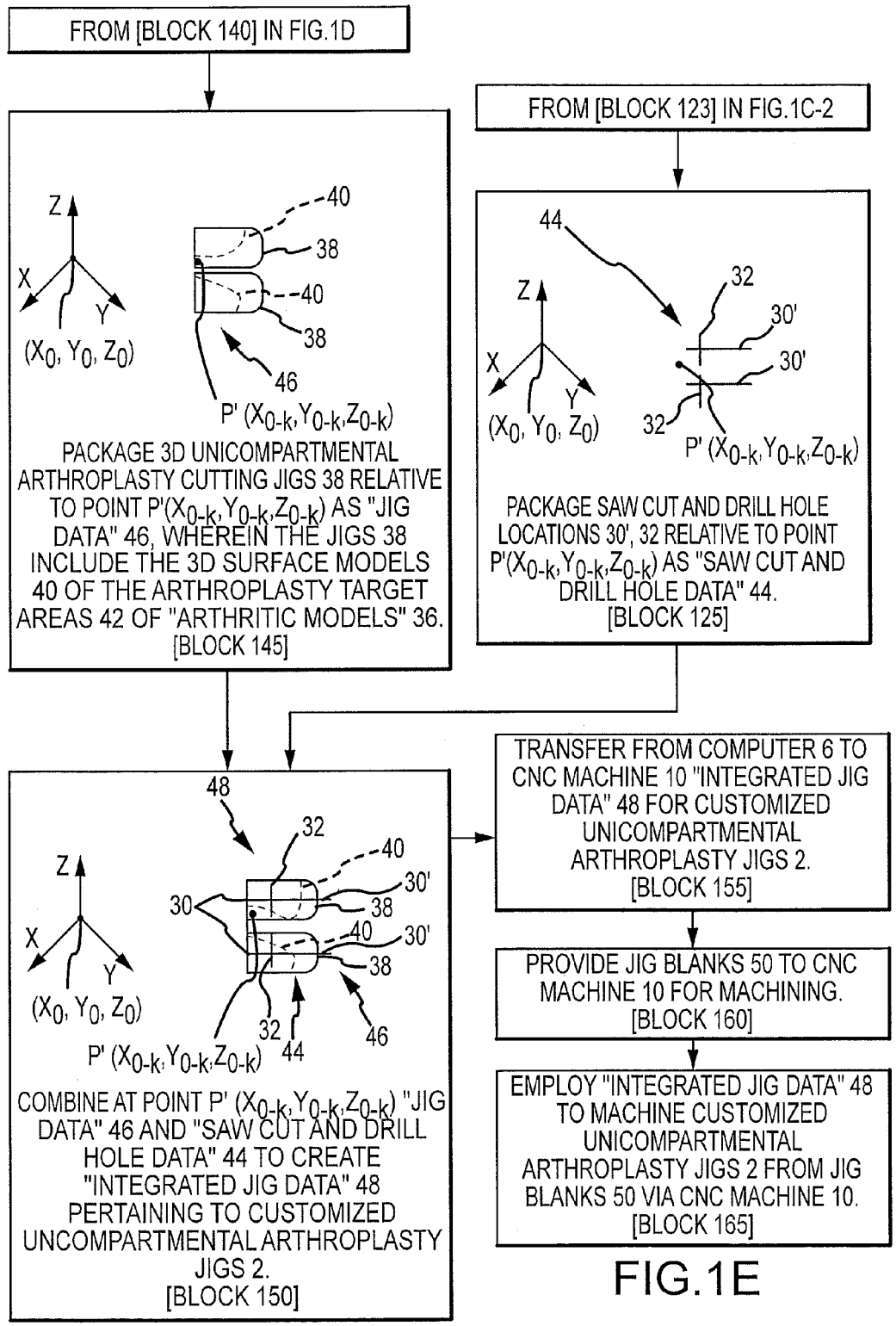

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 or other rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state or natural alignment state.

As shown in FIG. 1A, the system 4 includes a computer 6 having a CPU 8, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C-1, the 2D images 16 are employed to create computer generated 3D bone-only (i.e., "bone models") 22 of the bones 18, 20 forming the patient's joint 14 [block 110]. The bone models 22 are located such that point P is at coordinates ($X_{0-j}$, $Y_{0-j}$, $Z_{0-j}$) relative to an origin ($X_0$, $Y_0$, $Z_0$) of an X—Y—Z axis [block 110]. The bone models 22 depict the bones 18, 20 in the present deteriorated condition with their respective degenerated joint surfaces 24, 26, which may be a result of osteoarthritis, injury, a combination thereof, etc. The degeneration may be minimal such that it is cartilage damage only and no bone damage. Alternatively, the degeneration may be more significant such that the damage is both to the cartilage and the bone.

In one embodiment, the bone surface contour lines of the bones 18, 20 depicted in the image slices 16 may be auto segmented via an image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

Computer programs for creating the 3D computer generated bone models 22 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1C-1, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_{0-j}$, $Y_{0-j}$, $Z_{0-j}$) relative to the origin ($X_0$, $Y_0$, $Z_0$). Thus, the restored bone models 28 share the same orientation and positioning relative to the origin ($X_0$, $Y_0$, $Z_0$) as the bone models 22. If damage is minimal to the bone (e.g., the damage is to the cartilage, only), the bone model 22 may not need much, if any, restoration, and the bone model 22 may be used as the restored bone model 28 for purposes of the process described herein.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the above-described bone restoration process is generally or completely automated, as disclosed in U.S. patent application Ser. No. 12/111,924 to Park, which is entitled Generation of a Computerized Bone Model Representative of a Pre-Degenerated State and Usable in the Design and Manufacture of Arthroplasty Devices, was filed Apr. 29, 2008 and is incorporated by reference in its entirety into this Detailed Description. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1C-1, the restored bone models 28 are employed in a pre-operative planning ("POP") procedure to determine saw cut locations 30 and drill hole locations 32 in the patient's bones that will allow the arthroplasty joint implants to generally restore the patient's joint line to its pre-degenerative alignment [block 120].

In one embodiment, the POP procedure is a manual process, wherein computer generated 3D uni-compartmental implant models 34 (e.g., femur and tibia implants in the context of the joint being a knee) and restored bone models 28 are manually manipulated relative to each other by a person sitting in front of a computer 6 and visually observing the uni-compartmental implant models 34 and restored bone models 28 on the computer screen 9 and manipulating the models 28, 34 via the computer controls 11. By superimposing the uni-compartmental implant models 34 over the restored bone models 28, or vice versa, the joint surfaces of the uni-compartmental implant models 34 can be aligned or caused to correspond with the joint surfaces of the restored bone models 28. By causing the joint surfaces of the models 28, 34 to so align, the uni-compartmental implant models 34 are positioned relative to the restored bone models 28 such that the saw cut locations 30 and drill hole locations 32 can be determined relative to the restored bone models 28.

Figure 1F:
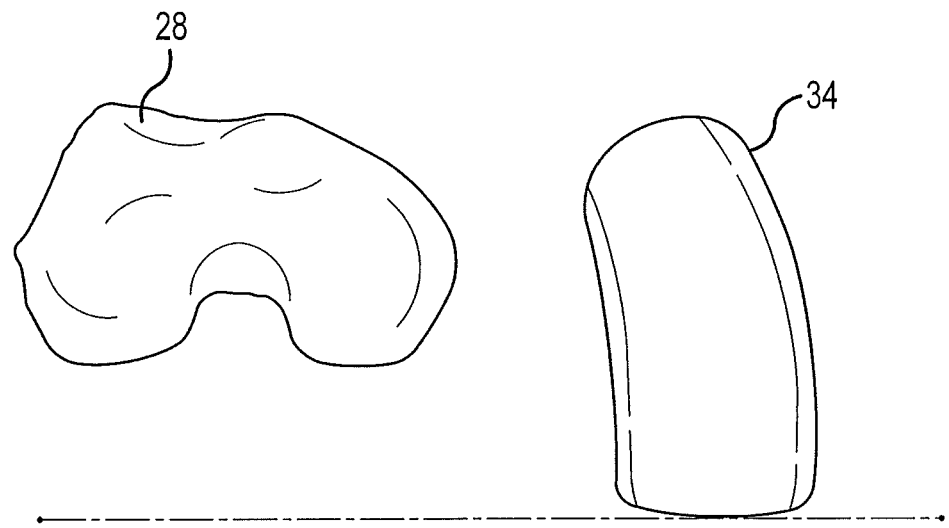
FIG. 1F is a distal axial view of the three dimensional ("3D") restored femoral bone model and the 3D femoral unicompartmental implant model adjacent to each other.
Figure 1G:
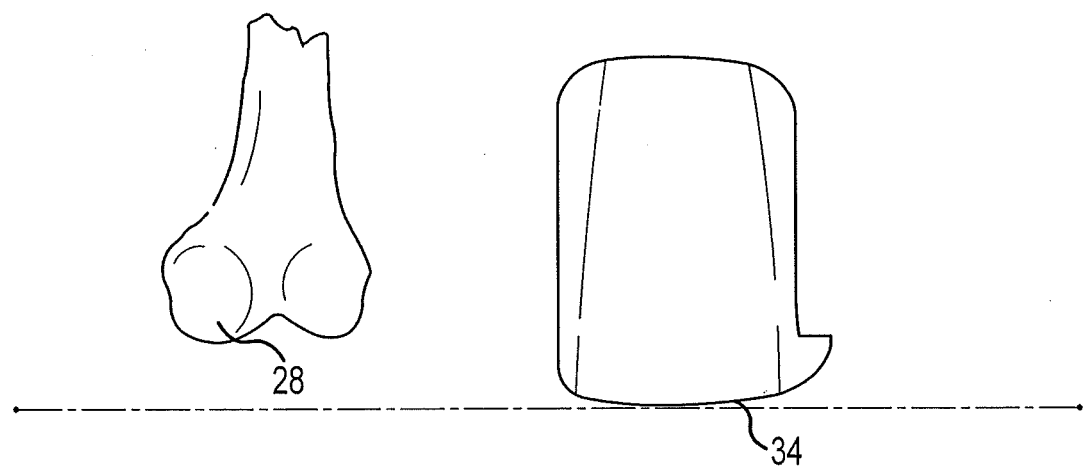
FIG. 1G is a posterior coronal view of the three dimensional ("3D") restored femoral bone model and the 3D femoral unicompartmental implant model adjacent to each other.
Figure 1H:
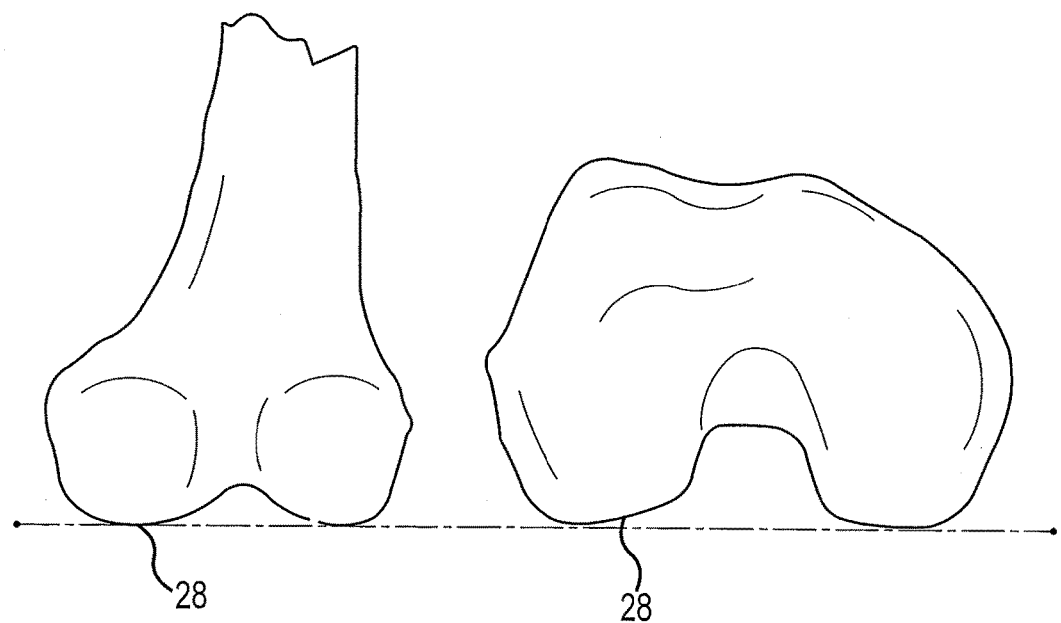
FIG. 1H illustrates adjacent posterior coronal and distal axial views of the 3D restored femoral bone model.
Figure 1I:
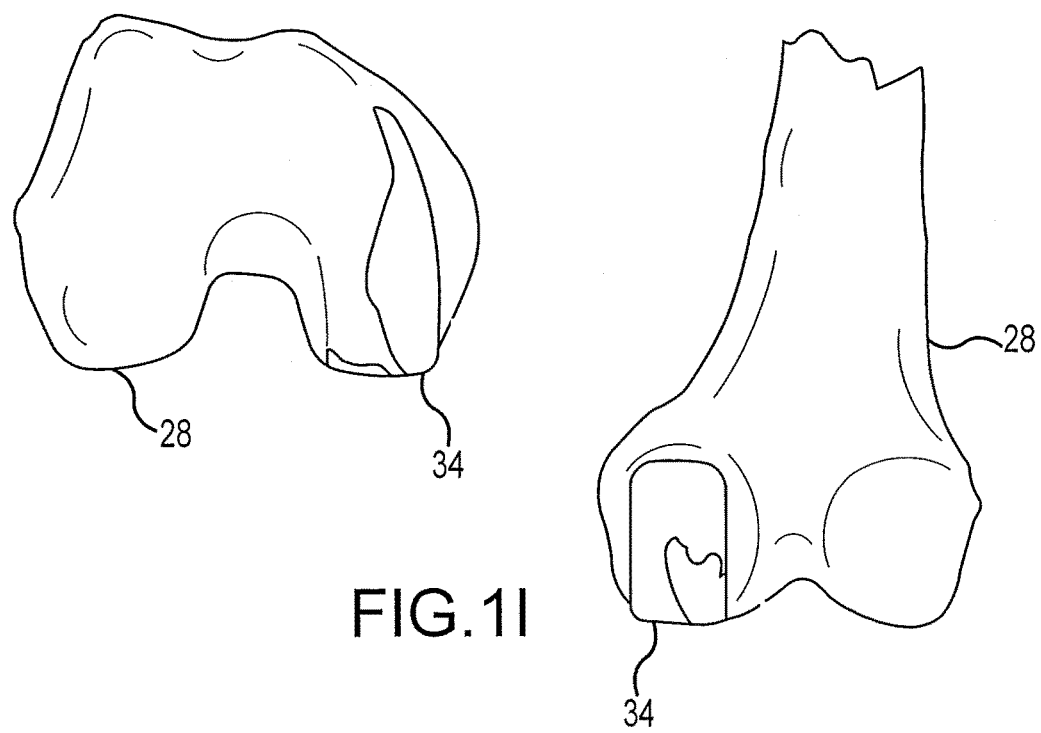
FIG. 1I illustrates the same adjacent views of the 3D restored femoral bone model as depicted in FIG. 1H, except the 3D femoral unicompartmental implant model is shape matched to the 3D restored femoral bone model.

In one embodiment, the POP process is generally or completely automated. For example, a computer program may manipulate computer generated 3D uni-compartmental implant models 34 (e.g., femur and tibia implants in the context of the joint being a knee) and restored bone models or planning bone models 28 relative to each other to determine the saw cut and drill hole locations 30, 32 relative to the restored bone models 28. With reference to the above POP discussion, in one embodiment, 3D models such as those depicted in FIGS. 1F-1M are created by a computer during POP. In one embodiment, the femur is planned first. As shown in FIGS. 1F-1G, which depict distal axial and posterior coronal views, respectively, the femoral restored bone model 28 and uni-compartmental femoral implant model 34 are generated by a computer during POP. As can be understood from FIGS. 1F-1H, the femoral restored bone model 28 is moved to the implant model 34 such that the articular surfaces of the models 28, 34 are superimposed or shape matched. Specifically, as depicted in FIG. 1I, the femoral restored bone model 28 may be moved such that the most posterior point and most distal point of the articular surface of the restored bone model are aligned relative to the posterior and distal planes that are respectively tangent to the most posterior point and most distal point of the articular surface of the femoral implant model 34. The articular surfaces of the implant model 34 may then be shape matched or superimposed on the articular surfaces of the femur model 28. While this discussion takes place in the context of the bone model 28 being moved to the implant model 34, in other embodiments, the reverse may be true.

Figure 1J:
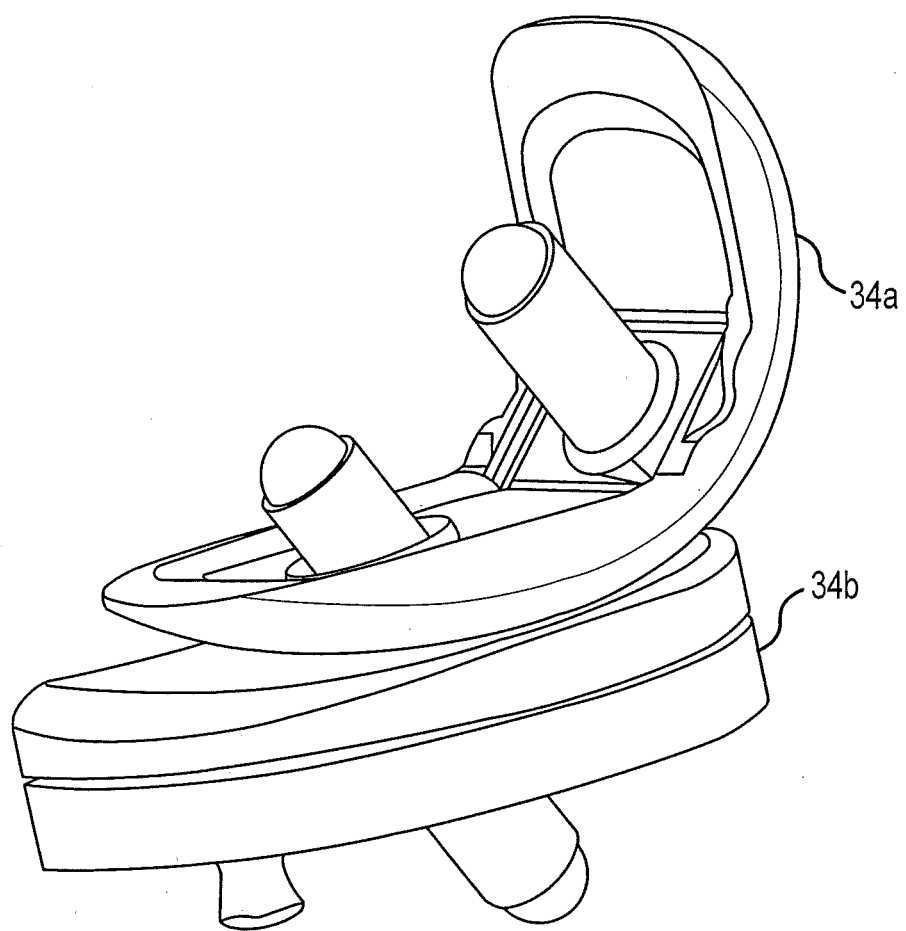
FIG. 1J is an isometric view of the 3D femoral and tibial unicompartmental implant models interfaced with each other.

As indicated in FIG. 1J, the femur implant model 34a and the tibia implant model 34b may be shown in a non-implanted state, which may help the planner visualize the spatial relationship between the implant models 34.

Figure 1K:
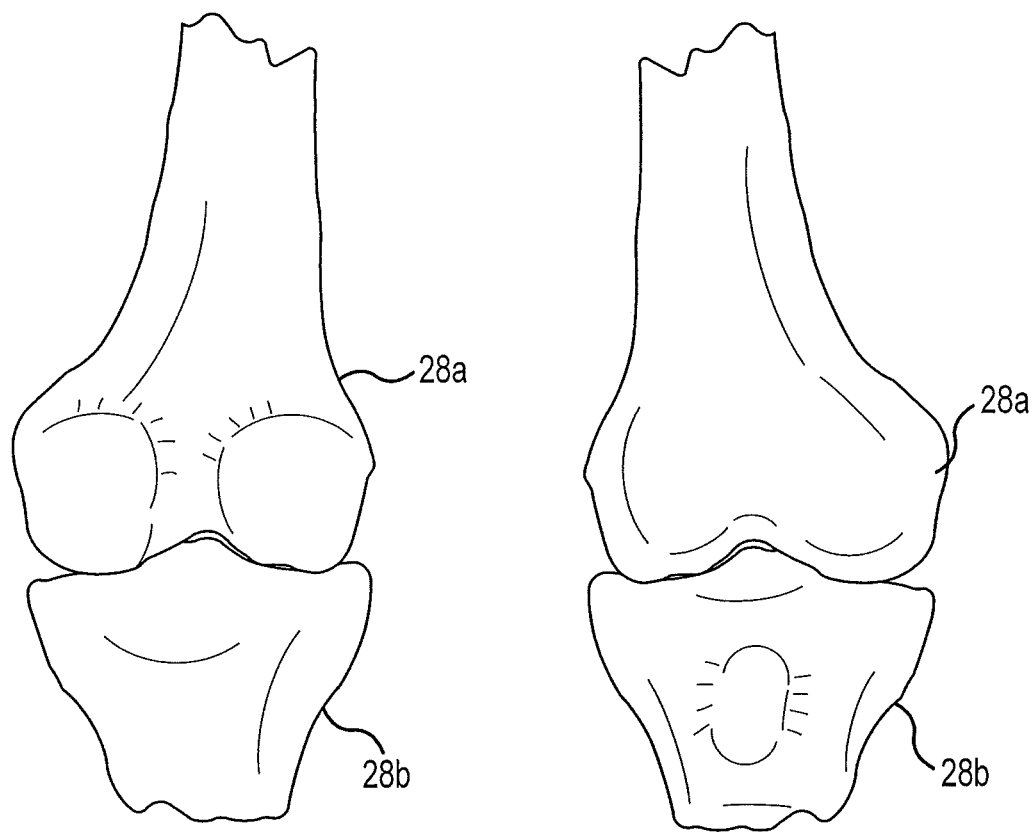
FIG. 1K illustrates adjacent posterior coronal and anterior coronal views of the 3D restored femoral and tibial bone models interfaced with each other.
Figure 1L:
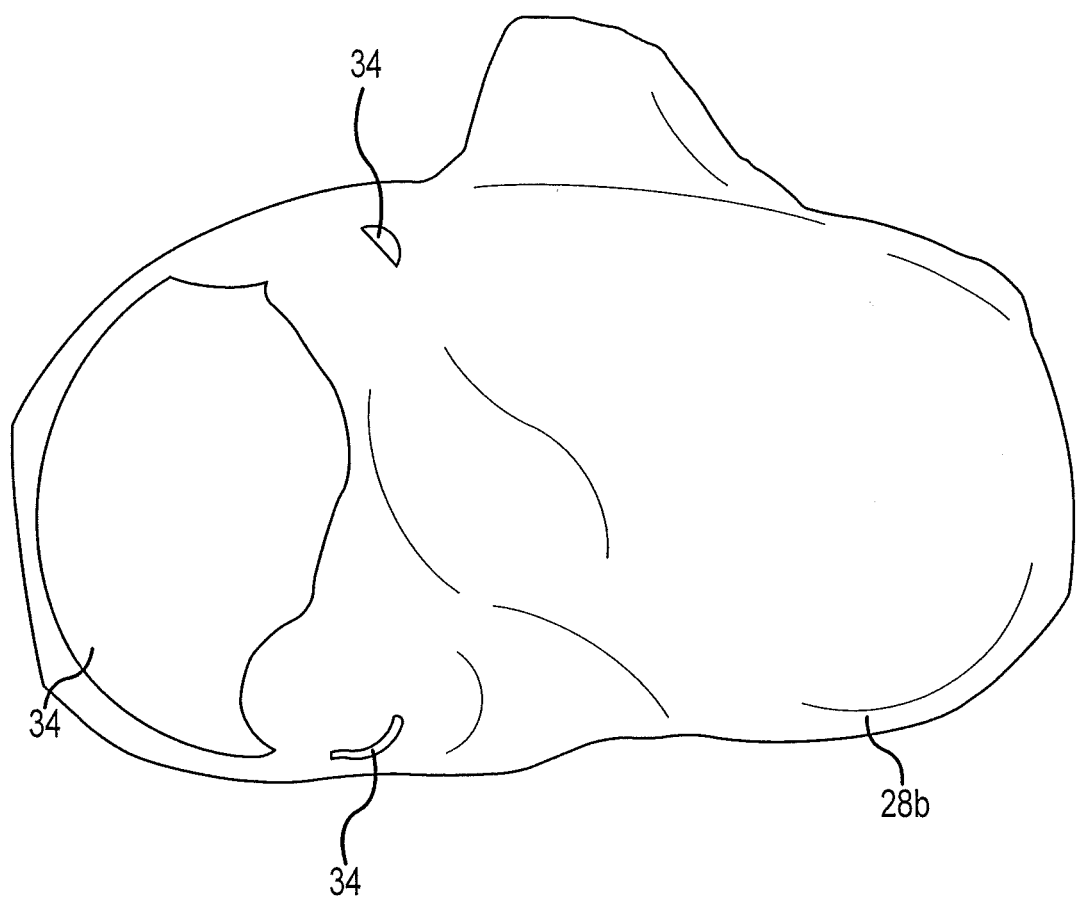
FIG. 1L illustrates a proximal axial view of the 3D restored tibial bone model with the 3D tibial unicompartmental implant model shape matched thereto.
Figure 1M:
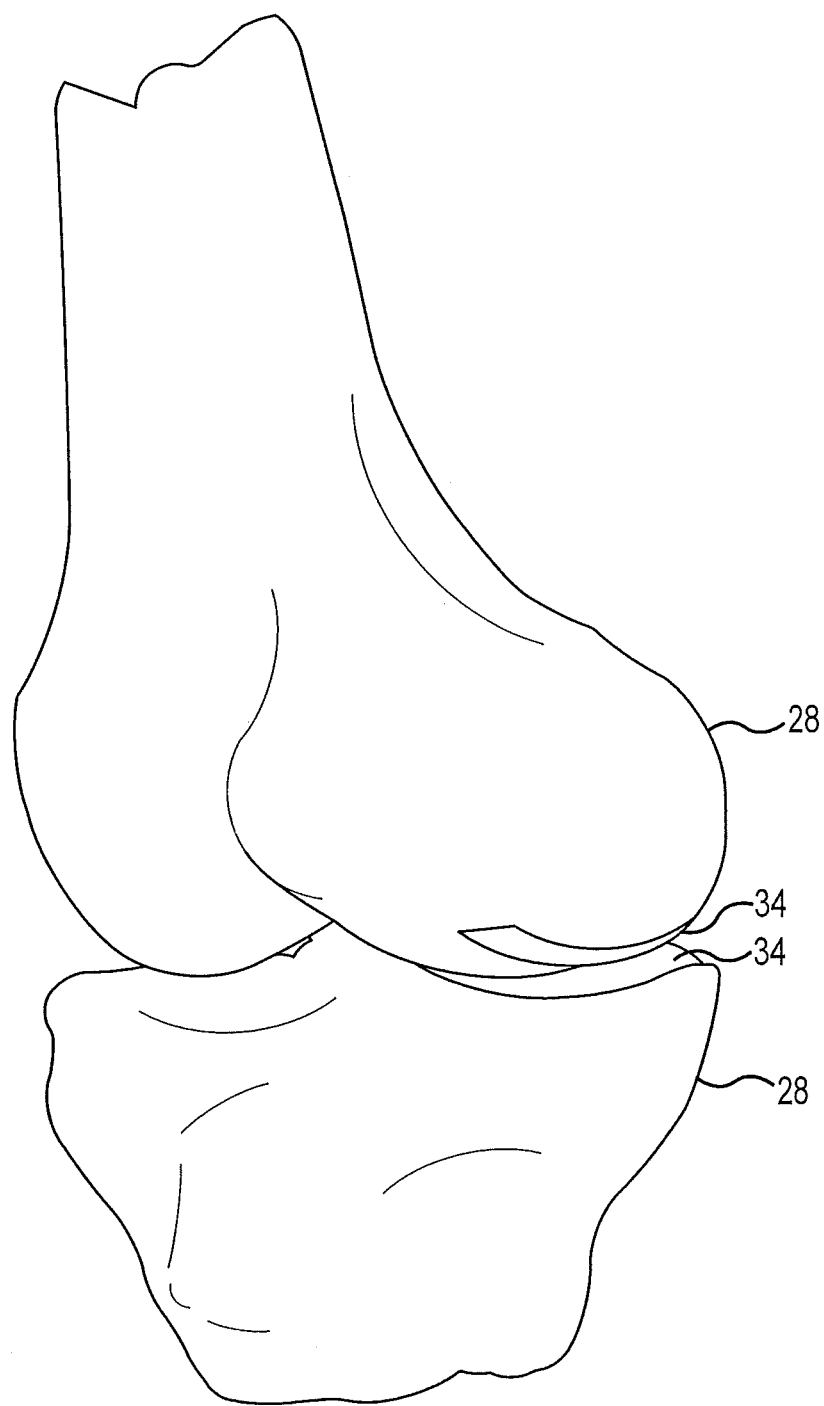
FIG. 1M is a coronal-sagital view of the 3D restored femoral and tibial bone models interfaced with each other.

The tibia is planned next. FIG. 1K illustrates the alignment of the tibia bone model 28b relative to the femoral bone model 28a, such that the femoral condyles are in contact with the tibial plateau. This determines the rotation of the tibia relative to the femur. Once tibial positioning is set, the tibial implant model 34 is displayed and changes to the tibial positioning are made to maximize shape matching (FIG. 1L). Sizing and appropriate off-set are accounted for. Then, the implant models 34 may be checked for proper alignment, as shown in FIG. 1M.

In summary and regardless of whether via the manual or the substantially or totally automated POP process, in one embodiment, the uni-compartmental implant models 34 may be superimposed over the restored bone models 28, or vice versa. In one embodiment, the uni-compartmental implant models 34 are located at point P' $(X_{0-k}, Y_{0-k}, Z_{0-k})$ relative to the origin $(X_0, Y_0, Z_0)$, and the restored bone models 28 are located at point P $(X_{0-j}, Y_{0-j}, Z_{0-j})$. To cause the joint surfaces of the models 28, 34 to correspond, the computer program may move the restored bone models 28 from point P $(X_{0-j}, Y_{0-j}, Z_{0-j})$ to point P' $(X_{0-k}, Y_{0-k}, Z_{0-k})$, or vice versa. Once the joint surfaces of the models 28, 34 are in close proximity, the joint surfaces of the uni-compartmental implant models 34 may be shape-matched to align or correspond with the joint surfaces of the restored bone models 28. By causing the joint surfaces of the models 28, 34 to so align, the uni-compartmental implant models 34 are positioned relative to the restored bone models 28 such that the saw cut locations 30 and drill hole locations 32 can be determined relative to the restored bone models 28.

In one embodiment, once the shape matching is achieved as discussed above with respect to [block 120], the implant model 34 is modified or positionally adjusted to achieve the proper spacing between the femur and tibia implants to account for the cartilage thickness not represented in the restored bone model 28. To achieve the correct adjustment, an adjustment value $T_r$ may be determined. The adjustment value $T_r$ that is used to adjust the surface matching may be based off of an analysis associated with the cartilage thickness. In one embodiment, the minimum cartilage thickness is observed and measured for the undamaged and damaged femoral condyle. If the greatest cartilage loss is identified on the surface of the healthy condyle, which is the medial condyle in this example, then the lateral condyle can be used as the cartilage thickness reference for purposes of POP and, more specifically, for the adjustment value $T_r$. Of course, where the lateral condyle is deteriorated and is the target of the uni-compartmental arthroplasty, then the cartilage thickness can be measured off of the healthy medial side condyle to determine adjustment value $T_r$. Thus, the adjustment value $T_r$ may be based on the cartilage thickness measured for the least damaged condyle cartilage. Once the adjustment value $T_r$ is determined based off of healthy side cartilage thickness, the femoral implant model 34 can be positionally adjusted or otherwise modified relative to the restored bone model 28 to account for cartilage thickness to restore the joint line.

A similar adjustment process is also performed for the proximal tibia such that the adjustment value $T_r$ is determined based off of cartilage thickness of the healthy side of the proximal tibia and the tibia implant model 34 can be positionally adjusted or otherwise modified relative to the restored bone model 28 to account for cartilage thickness to restore the joint line.

Thus, as can be understood from [block 123] of FIG. 1C-2, once the shape matching process of the POP in [block 120] has been achieved to align the articular surfaces of the implant models 34 relative to the articular surfaces of the restored bone models 28, the implant models 34 may be adjusted relative to the bone models 28 to account for the cartilage thickness not represented in the bone only models 28. Specifically, in one embodiment, the femur implant model 34 or its saw cut plane 30 may be shifted distally relative to the restored femur bone model 28 a distance equal to the adjustment value $T_r$, which is obtained from the thickness of the healthy side condyle and thereby creating a shifted femur implant model 34' or shifted saw cut plane 30' [block 123]. Similarly, the tibia implant model 34 or its saw cut plane 30 may be shifted distally relative to the restored tibia bone model 28 a distance equal to the adjustment value $T_r$, which is obtained from the thickness of the healthy side condyle and thereby creating a shifted tibia implant model 34' or shifted saw cut plane 30' [block 123]. A more detailed discussion of the POP procedure is disclosed in U.S. Provisional Patent Application 61/102,692 to Park, which is entitled Arthroplasty System and Related Methods, was filed Oct. 3, 2008 and is incorporated by reference in its entirety into this Detailed Description.

As indicated in FIG. 1E, in one embodiment, once the saw cut planes 30' have been adjusted for the adjustment value $T_r$ as set out in [block 123], the data 44 regarding the saw cut and drill hole locations 30', 32 relative to point P' $(X_{0-k}, Y_{0-k}, Z_{0-k})$ is packaged or consolidated as the "saw cut and drill hole data" 44 [block 125]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C-1 are also used to create computer generated 3D bone and cartilage models (i.e., "arthritic models") 36 of the bones 18, 20 forming the patient's joint 14 [block 130] Like the above-discussed bone models 22, the arthritic models 36 are located such that point P is at coordinates $(X_{0-j}, Y_{0-j}, Z_{0-j})$ relative to the origin $(X_0, Y_0, Z_0)$ of the X—Y—Z axis [block 130]. Thus, the bone and arthritic models 22, 36 share the same location and orientation relative to the origin $(X_0, Y_0, Z_0)$. This position/orientation relationship is generally maintained throughout the process discussed with respect to FIGS. 1B-1E. Accordingly, movements relative to the origin $(X_0, Y_0, Z_0)$ of the bone models 22 and the various descendants thereof (i.e., the restored bone models 28, bone cut locations 30, and drill hole locations 32, although not with respect to the correction of bone cut locations 30, with respect to adjustment value $T_r$ to arrive at the shifted cut locations 30' adjusted for cartilage thickness $T_r$) are also applied to the arthritic models 36 and the various descendants thereof (i.e., the uni-compartmental jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 22, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty uni-compartmental jig models 38 [block 140]. Thus, the uni-compartmental jig models 38 are configured or indexed to matingly receive the arthroplasty target areas 42 of the arthritic models 36. Jigs 2 manufactured to match such uni-compartmental jig models 38 will then matingly receive the arthroplasty target areas of the actual joint bones during the arthroplasty surgical procedure.

In one embodiment, the procedure for indexing the uni-compartmental jig models 38 to the arthroplasty target areas 42 is a manual process. The 3D computer generated models 36, 38 are manually manipulated relative to each other by a person sitting in front of a computer 6 and visually observing the uni-compartmental jig models 38 and arthritic models 36 on the computer screen 9 and manipulating the models 36, 38 by interacting with the computer controls 11. In one embodiment, by superimposing the uni-compartmental jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the uni-compartmental jig models 38, resulting in uni-compartmental jig models 38 indexed to matingly receive the arthroplasty target areas 42 of the arthritic models 36. Point P' ($X_{0-k}$, $Y_{0-k}$, $Z_{0-k}$) can also be imported into the uni-compartmental jig models 38, resulting in uni-compartmental jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the uni-compartmental jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the uni-compartmental jig models 38, resulting in the uni-compartmental jig models 38 being indexed to matingly receive the arthroplasty target areas 42 of the arthritic models 36. The resulting uni-compartmental jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 1E, in one embodiment, the data regarding the uni-compartmental jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or natural alignment state.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

The remainder of this Detailed Description will now discuss example customized arthroplasty uni-compartmental cutting jigs 2 capable of being manufactured via the above-discussed process in addition to methods of using the jigs 2. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 2A-18B are for partial knee ("uni-compartmental") replacement procedures. Thus, although the discussion provided herein is given in the context of uni-compartmental jigs and the generation thereof, this disclosure is readily applicable to total arthroplasty procedures in the knee or other joint contexts. Thus, the disclosure provided herein should be considered as encompassing jigs and the generation thereof for both total and uni-compartmental arthroplasty procedures.

Figure 2A:
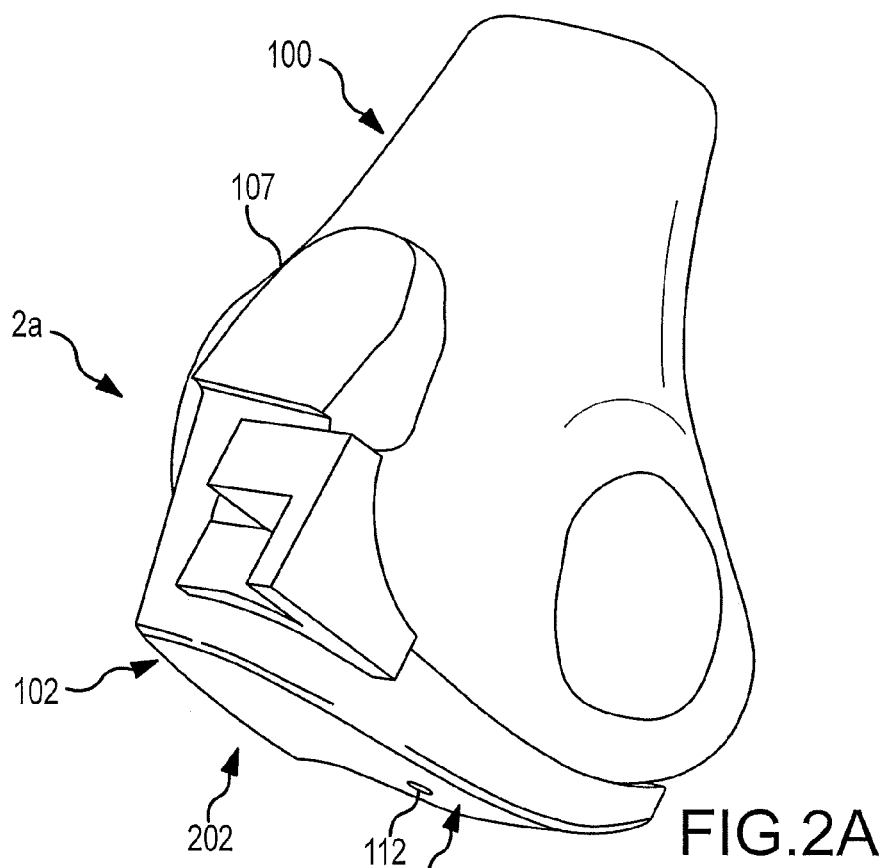
FIGS. 2A-2B are isometric views of a uni-compartmental femur arthroplasty jig that may be produced by the methods disclosed herein in a customized state, wherein the jig is shown either on (FIG. 2A) or off (FIG. 2B) the distal femur.
Figure 2B:
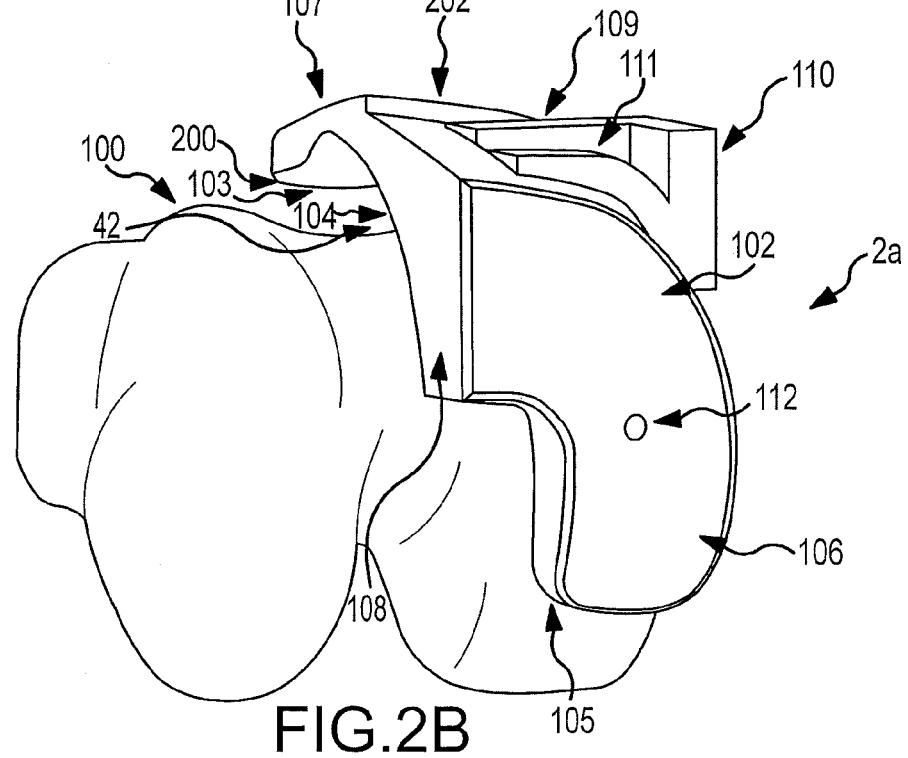
Figure 2C:
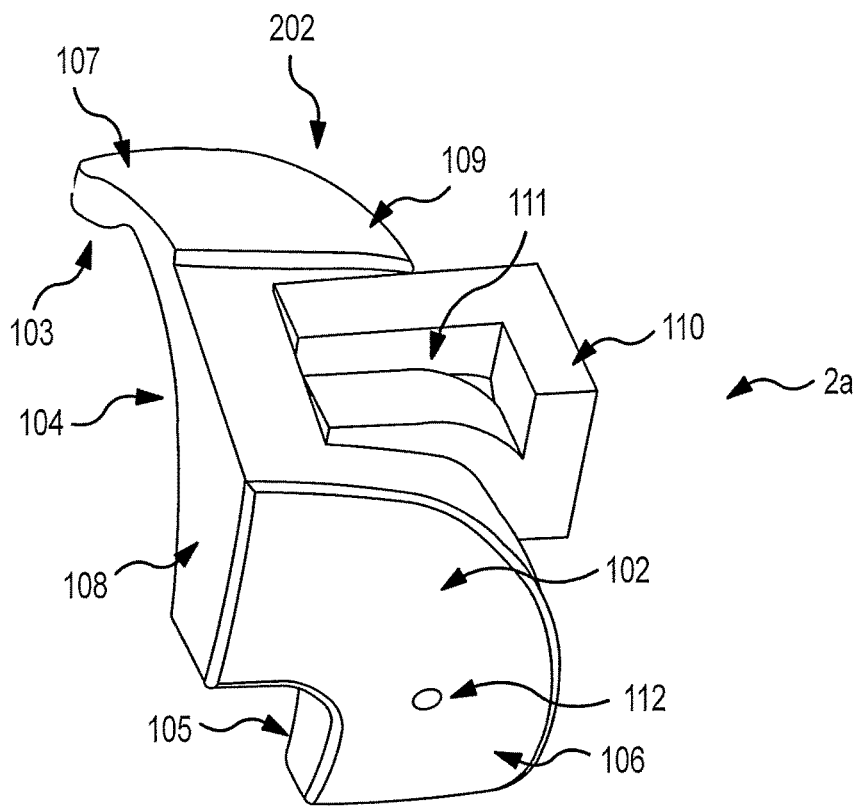
FIG. 2C depicts a top view of the uni-compartmental femur arthroplasty jig, wherein the femur is not shown, the jig being in a customized state.
Figure 2D:
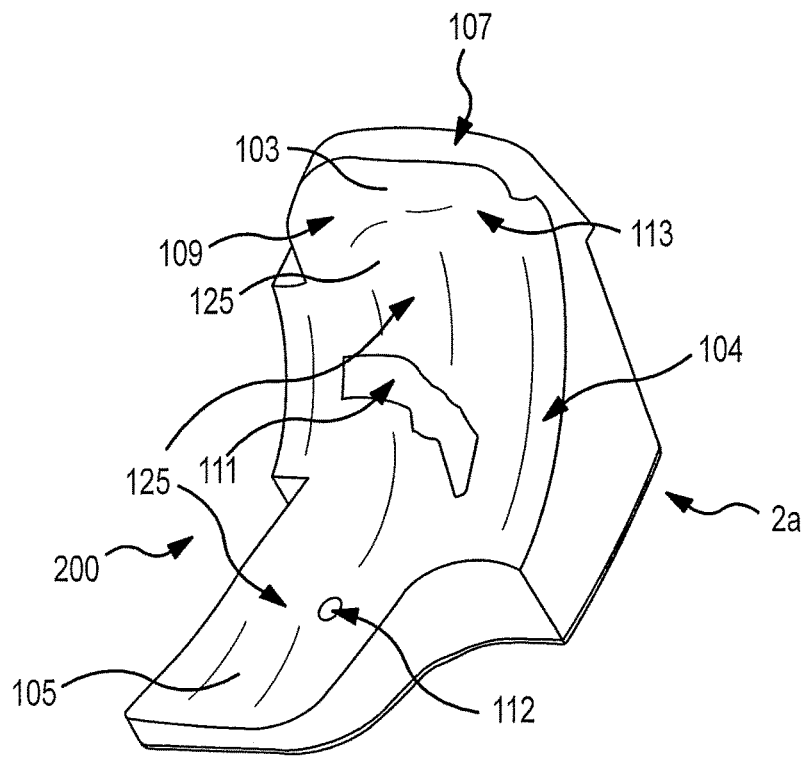
FIG. 2D depicts a bottom view of the uni-compartmental femur arthroplasty jig of FIG. 2C.
Figure 2E:
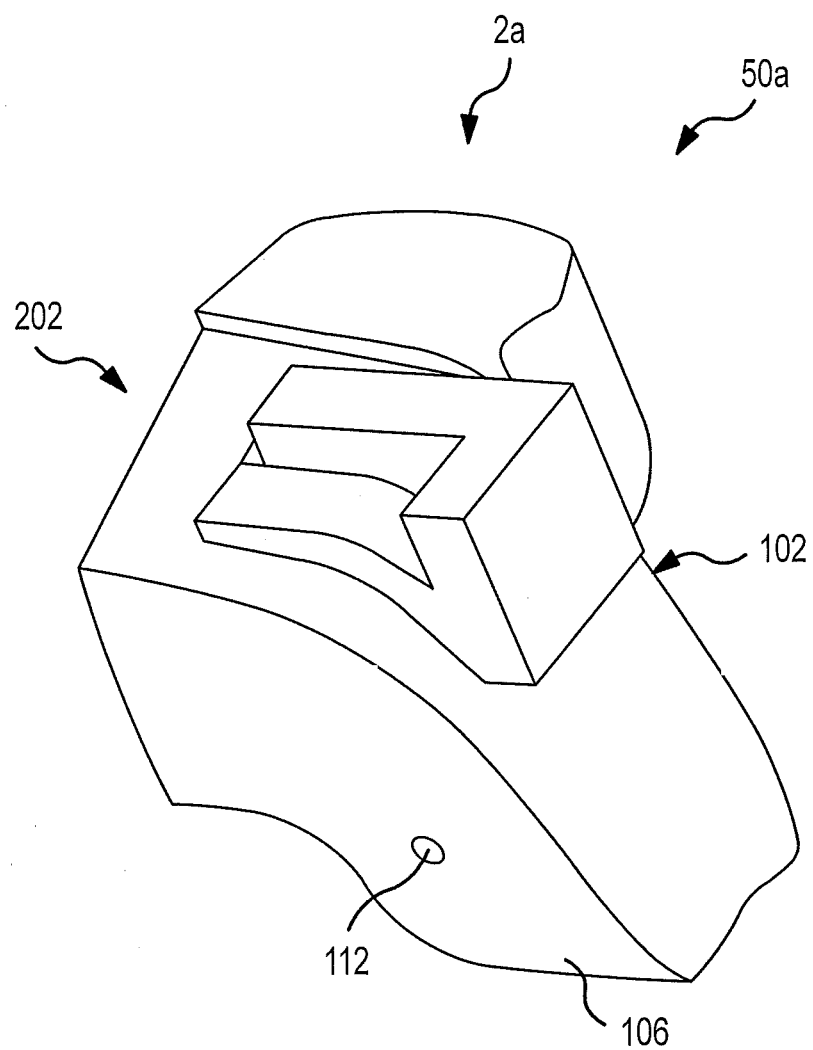
FIG. 2E depicts a top-side isometric view of the uni-compartmental femur arthroplasty jig of FIG. 2C, wherein the jig is in a non-customized state or, in other words, in the form of a jig blank from which the jig in manufactured.

For a discussion of a femur arthroplasty jig 2a, reference is first made to FIGS. 2A-2E. FIGS. 2A-2B are isometric views of the femur arthroplasty jig 2a in a customized state, wherein the jig 2A is shown either on (FIG. 2A) or off (FIG. 2B) the distal femur 100. FIGS. 2C-2D depict isometric top, bottom and side views of the femur arthroplasty jig 2a, wherein the femur 100 is not shown, the jig 2a being in a customized state. FIG. 2E is a side-top isometric view of the jig 2a in a non-customized state or, in other words, in the form of a jig blank 50a from which the jig 2a is manufactured.

As shown in FIGS. 2A-2E, a femur arthroplasty jig 2a may include an interior side or portion 200 and an exterior side or portion 202. When the femur cutting jig 2a is used in a UKA procedure, the interior side or portion 200 faces and matingly receives the arthroplasty target area 42 of the femur lower end, and the exterior side or portion 202 is on the opposite side of the femur cutting jig 2a from the interior portion 200.

As can be best understood from FIGS. 2B and 2D, the interior side 200 may include an anterior flange 107, a mid section 104, a distal cut slot 111, a distal drill hole 112, an antero-medial section 109, and a target area 125. In some embodiments, the target area 125 may include an anterior mating surface 103 and a distal condylar mating surface 105. The anterior mating surface may include a hooking portion 113. The interior portion 200 of the femur jig 2a is configured to match the surface features of the damaged lower end (i.e., the arthroplasty target area 42) of the patient's femur 18. Thus, when the arthroplasty target area 42 is received in the target area 125 of the interior portion 200 of the femur jig 2a during the UKA surgery, the surfaces of the target area 42 and the target area 125 of the interior portion 200 of the jig 2a match.

The surface of the interior portion 200 of the femur cutting jig 2A is machined or otherwise formed into a selected femur jig blank 50A and is based or defined off of a 3D surface model 40 of a target area 42 of the damaged lower end or target area 42 of the patient's femur 18.

As shown in FIGS. 2A, 2C and 2E, the exterior side 202 of the jig 2a may include an anterior flange 107, an anterior-distal condylar section 102 and a posterior-distal condylar section 106, a lateral edge 108, a mid section 104, a distal cut slot 111, a distal drill hole 112, and an antero-medial section 109. In some embodiments, the exterior side may also include a cut slot extension 110 for a close slot. The interior side 200 and the exterior side 202 help the jig 2a to mate stably and accurately to the distal femur, thereby accurately positioning the distal cut slot 111 that will be used to guide the distal cut of the medial condyle. The jig 2a also incorporates one or more distal drill holes 112 that may guide the positioning of a secondary cutting guide or "chamfer" block. This subsequently creates the cuts that will determine the flexion/extension, internal/external, anterior/posterior, distal/proximal position of the UKA implant. The medial/lateral position is left open.

Figure 3A:
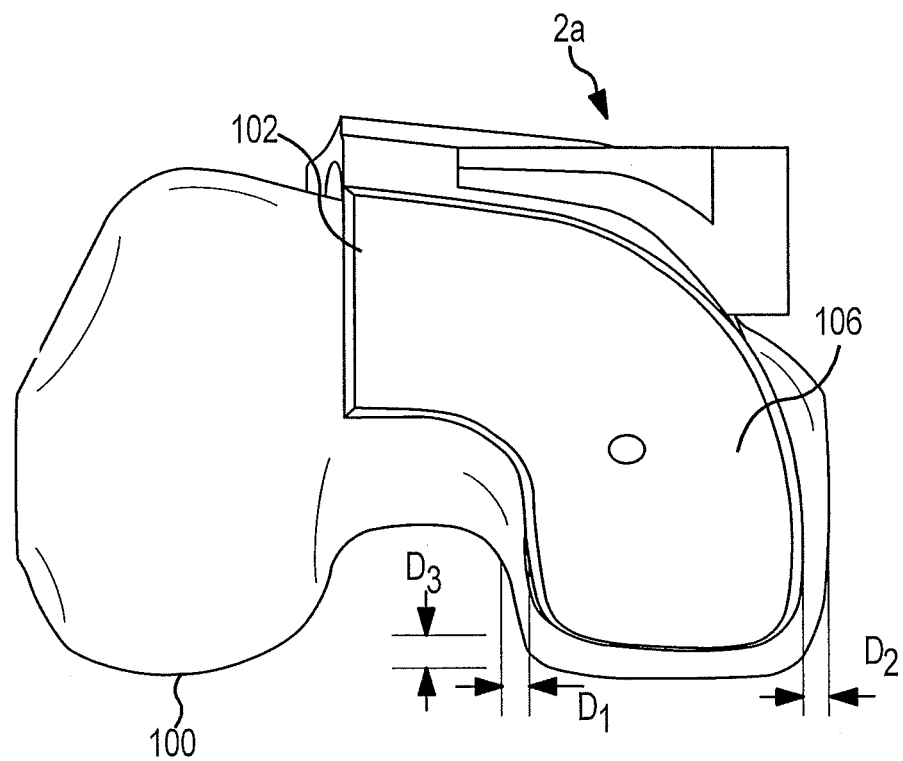
FIG. 3A illustrates how the uni-compartmental femur arthroplasty jig of FIG. 2A may be sized based on the medial condyle.
Figure 3B:
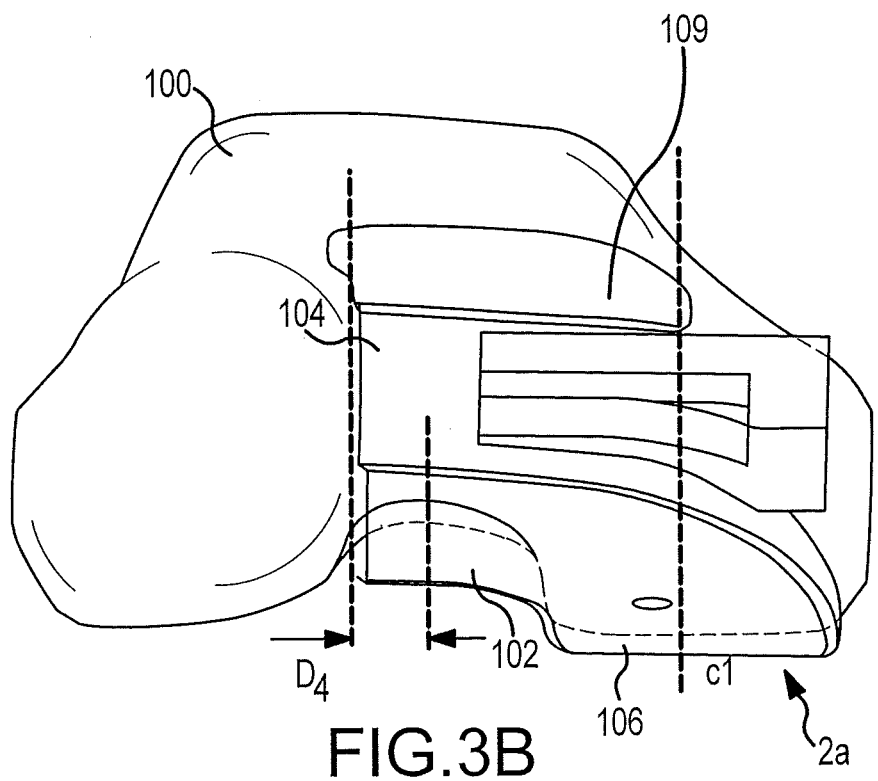
FIG. 3B illustrates the area in the trochlear groove and the anterior cortex that may be covered by the jig of FIG. 2A.
Figure 3C:
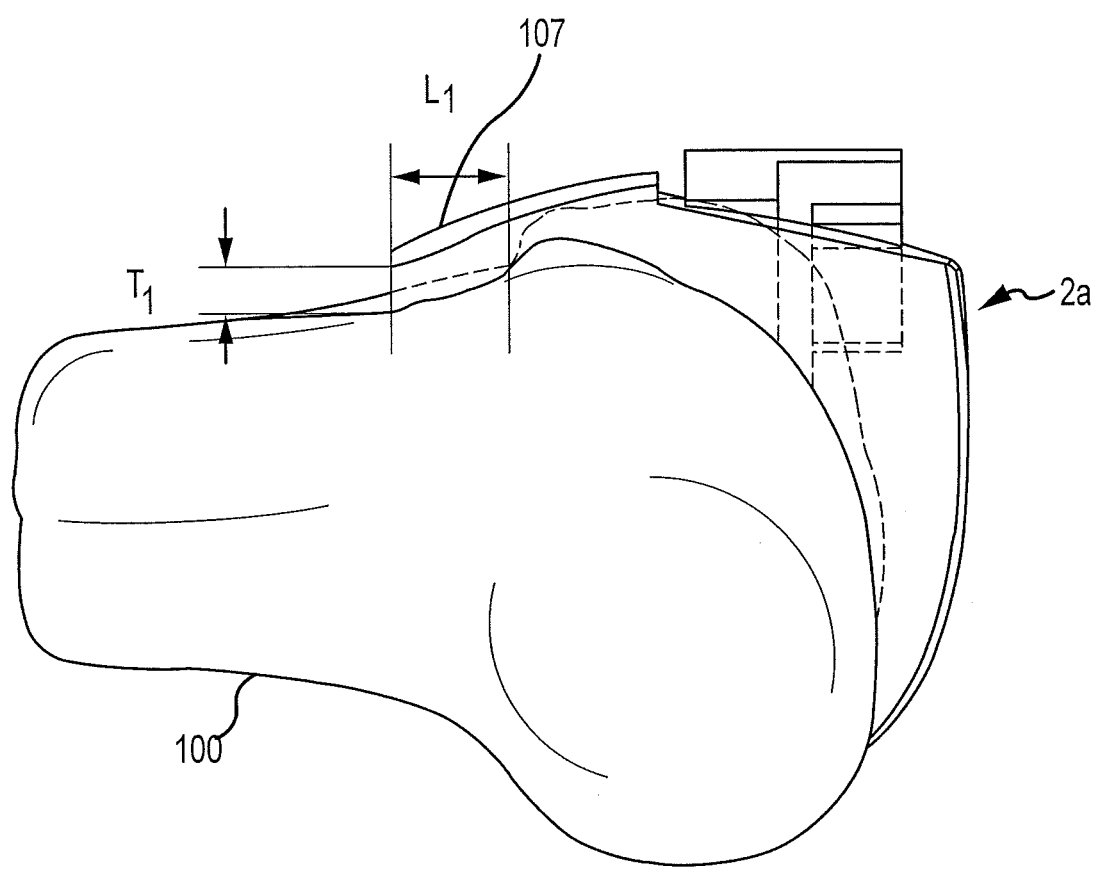
FIG. 3C illustrates how the size of the anterior flange of the jig of FIG. 2A may be determined.

For a discussion of certain sizing measurements that may be utilized in the development of the femur cutting jig 2a, reference is now made to FIGS. 3A-3C. FIG. 3A illustrates how the femur arthroplasty jig 2a of FIG. 2A may be sized based on the medial condyle. FIG. 3B illustrates the area in the trochlear groove and the anterior cortex that may be covered by the jig 2a of FIG. 2A. FIG. 3C illustrates how the size of the anterior flange 107 of the jig 2a of FIG. 2A may be determined.

The size of the femoral jig 2a depends on the size of each particular patient's bone. In one embodiment, as shown in FIGS. 3A-3C, the anterior-distal and posterior-distal condylar section 102,106 may be designed to reach within a distance $D_1$ and $D_2$ of approximately 2-3 mm of the medial and lateral ends of the medial condyle, and to reach within a distance $D_3$ of approximately 3-5 mm of the posterior condyle as shown in FIG. 3A. The mid section 104 should reach to within a distance $D_4$ of approximately 3-5 mm to the lateral side of the bottom of the trochlear groove as shown in FIG. 3B. The medial edge of the antero-medial section 109 should line up with a line c1 drawn from the middle of the medial condyle as shown in FIG. 3B. In one embodiment, the anterior flange 107 may have a thickness $T_1$ of approximately 5 mm or less and the top of the anterior flange 107 should have a length $L_1$ of approximately 0.8-1.2 mm of the target area as shown in FIG. 3C. In one embodiment, the thickness $T_1$ is 4 mm. The cut slot 111 may be positioned according to the position of the femoral implant, as described in more detail above.

Figure 6:
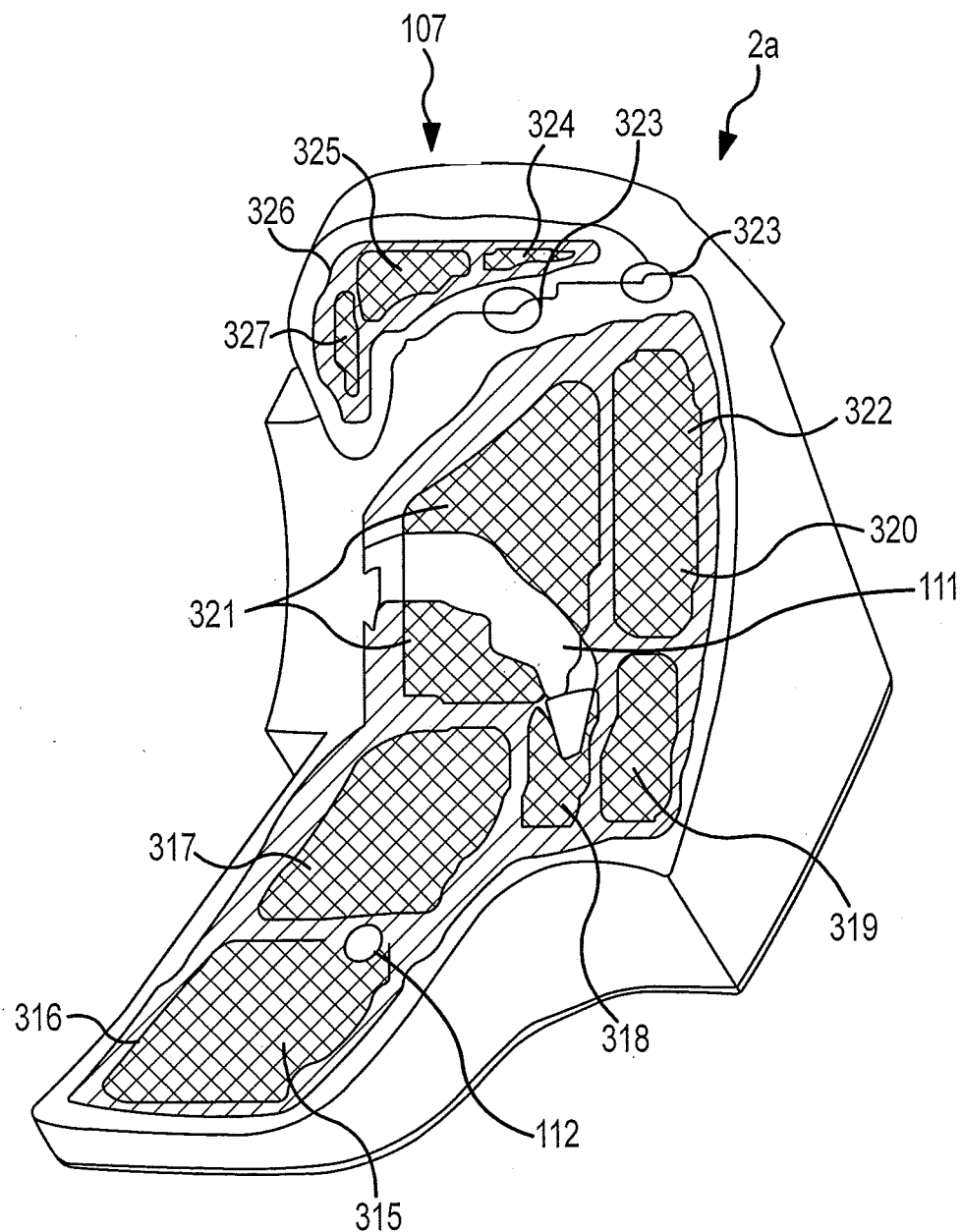
FIG. 6 is an isometric view of the uni-compartmental arthroplasty femur jig with mating surfaces corresponding to those of the distal femoral condyle depicted in FIGS. 4A and 4B.
Figure 7:
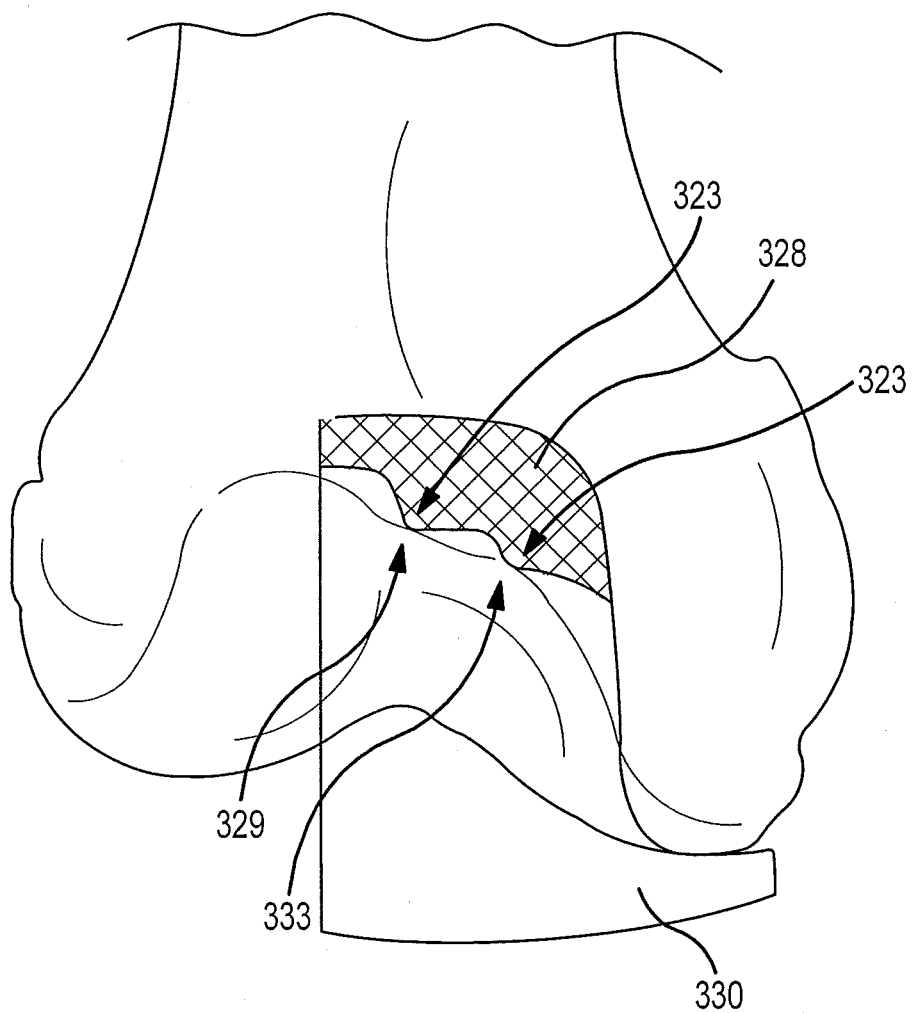
FIG. 7 illustrates mating and hooking of the anterior flange of the uni-compartmental arthroplasty femur jig about the edge of the anterior-proximal trochlear groove.
Figure 8:
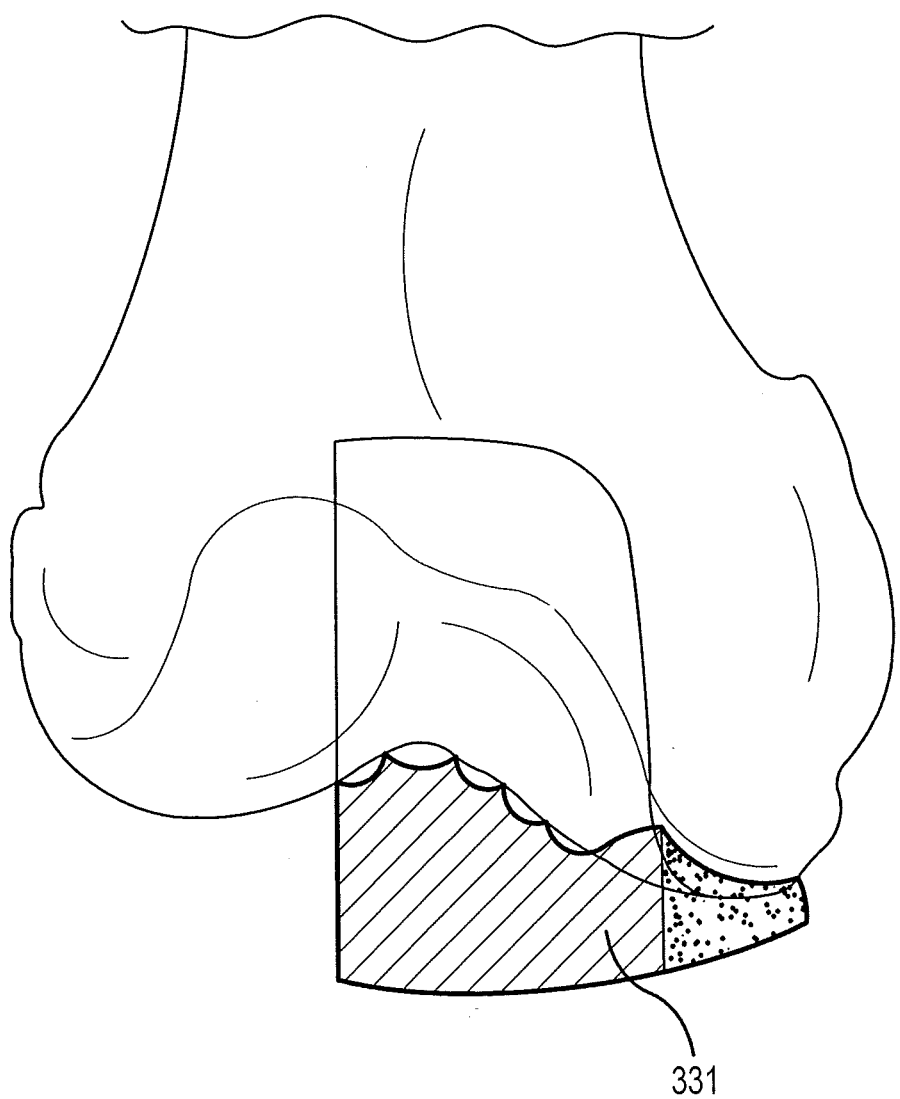
FIG. 8 illustrates one method of mating to the trochlear groove.
Figure 9:
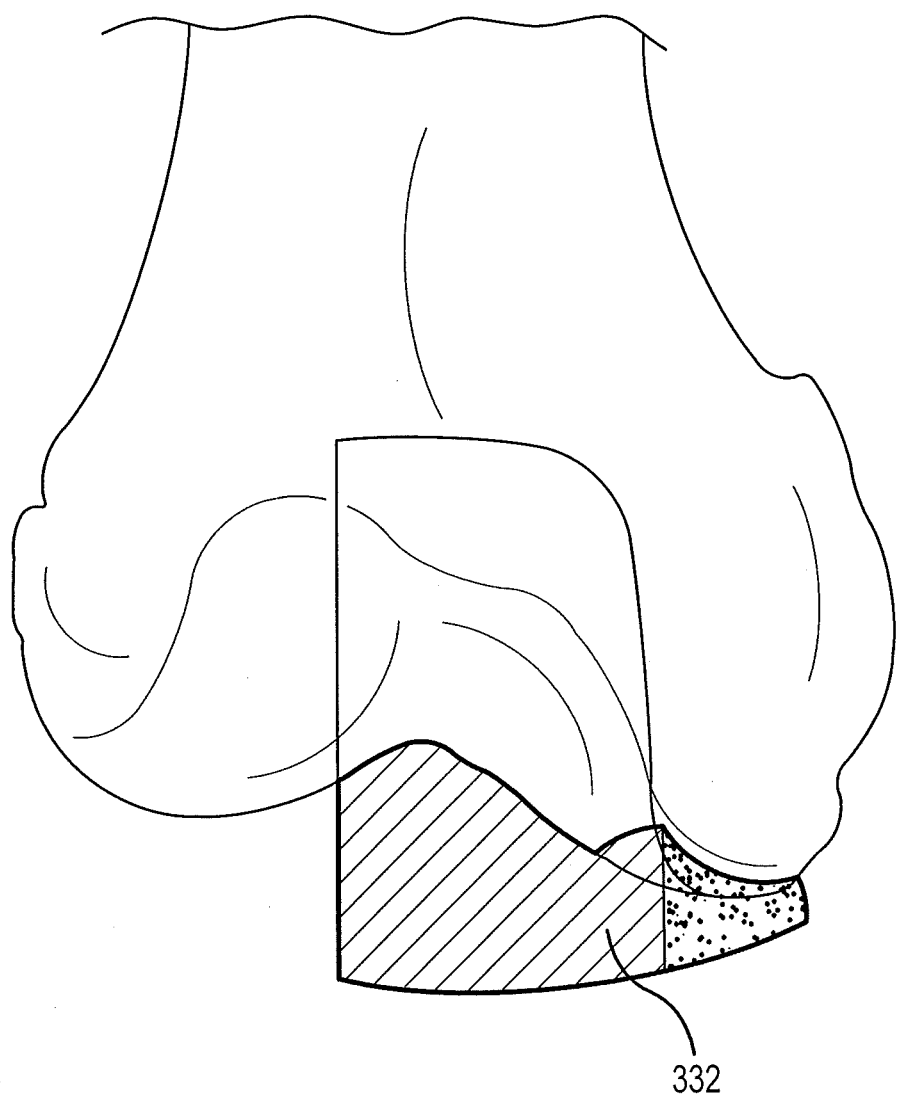
FIG. 9 illustrates full mating of the trochlear groove.
Figure 10:
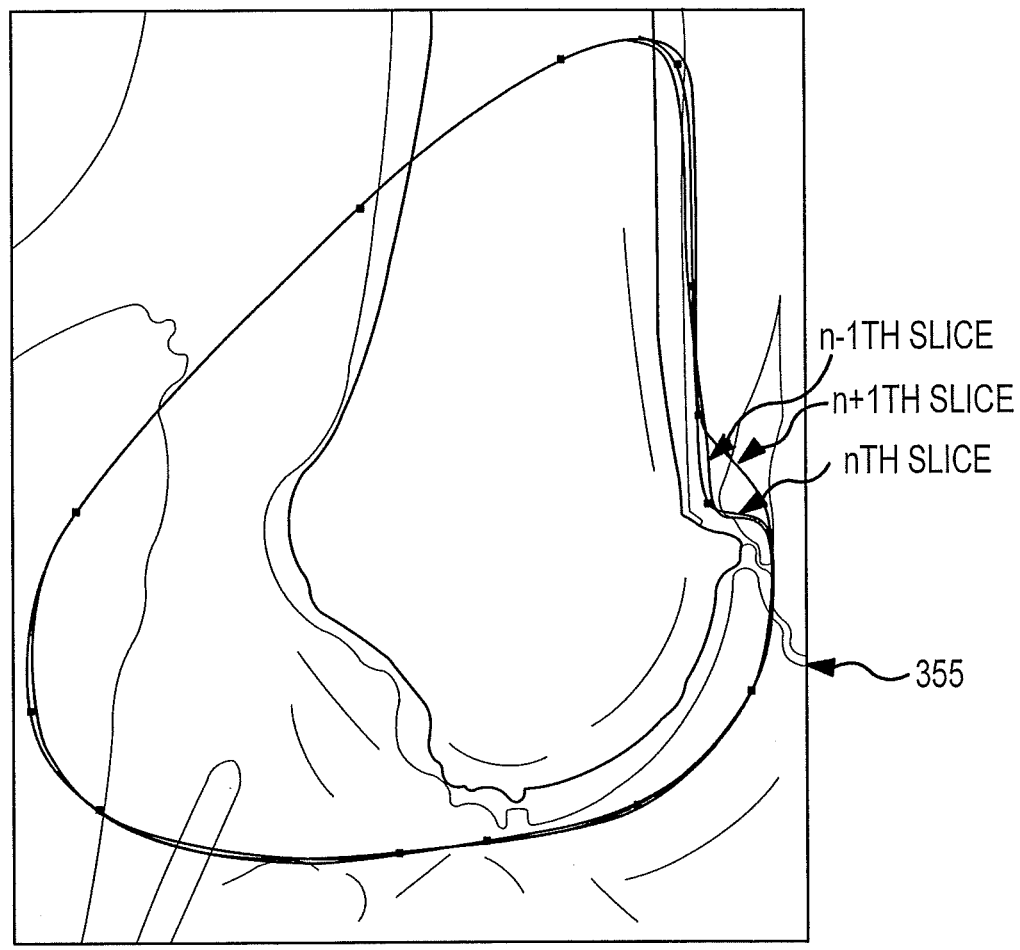
FIG. 10 illustrates a single MRI slice in the sagittal plane with three consecutive segmentation outlines where the corresponding outline hooks the edge of the anterior-proximal trochlear groove.

For a discussion of the mating surfaces for the femur arthroplasty jig 2a, reference is now made to FIGS. 4-10. FIGS. 4A and 4B display one embodiment of the mating surfaces for the arthroplasty femur jig 2a about the distal femoral condyle. FIGS. 5A and 5B display an embodiment having a reduced number of mating surfaces that still provides adequate stability of the arthroplasty femur jig 2a about the distal femoral condyle 350. FIG. 6 is an isometric view of the arthroplasty femur jig 2a with mating surfaces corresponding to those of the distal femoral condyle 350 depicted in FIGS. 4A and 4B. FIG. 7 illustrates mating and hooking of the anterior flange 107 of the arthroplasty femur jig 2a about the edge of the anterior-proximal trochlear groove. FIG. 8 illustrates one method of mating 331 to the trochlear groove. FIG. 9 illustrates full mating 332 of the trochlear groove. FIG. 10 illustrates a single MRI slice 355 in the sagittal plane with three consecutive segmentation outlines where the corresponding outline hooks the edge of the anterior-proximal trochlear groove.

Figure 4A:
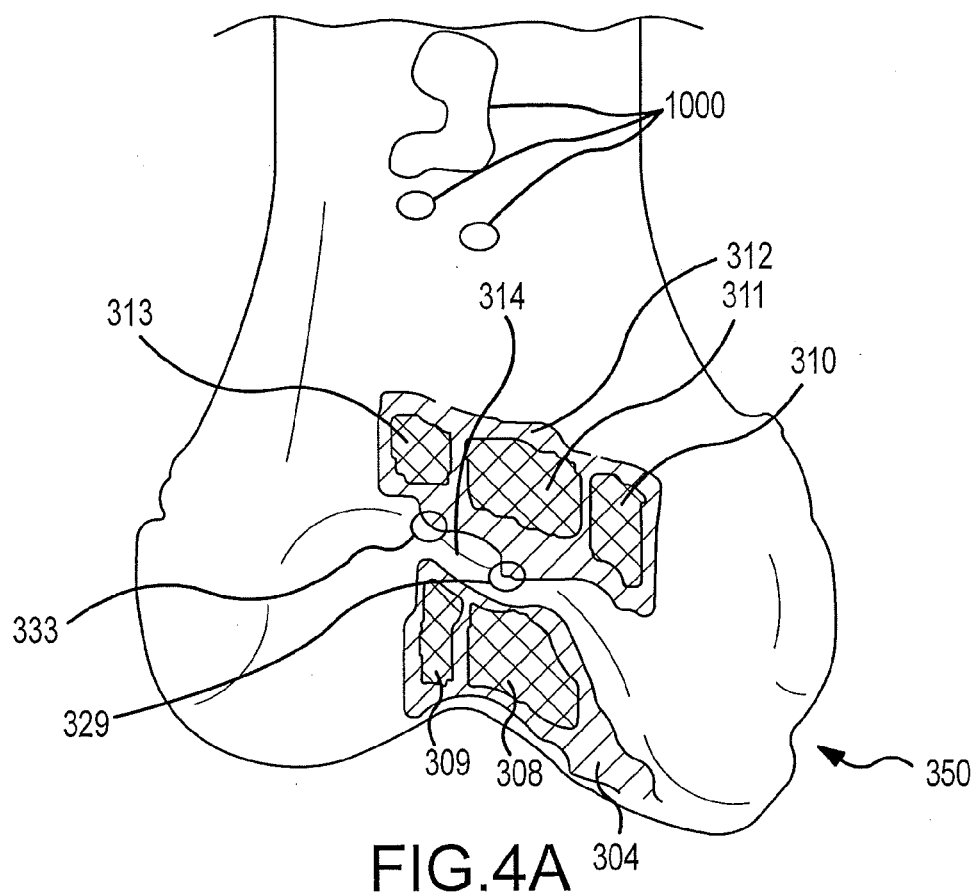
FIGS. 4A and 4B are, respectively, coronal and distal views of the femoral condyles and displaying one embodiment of the mating surfaces for the uni-compartmental arthroplasty femur jig about the distal femoral condyle.
Figure 4B:
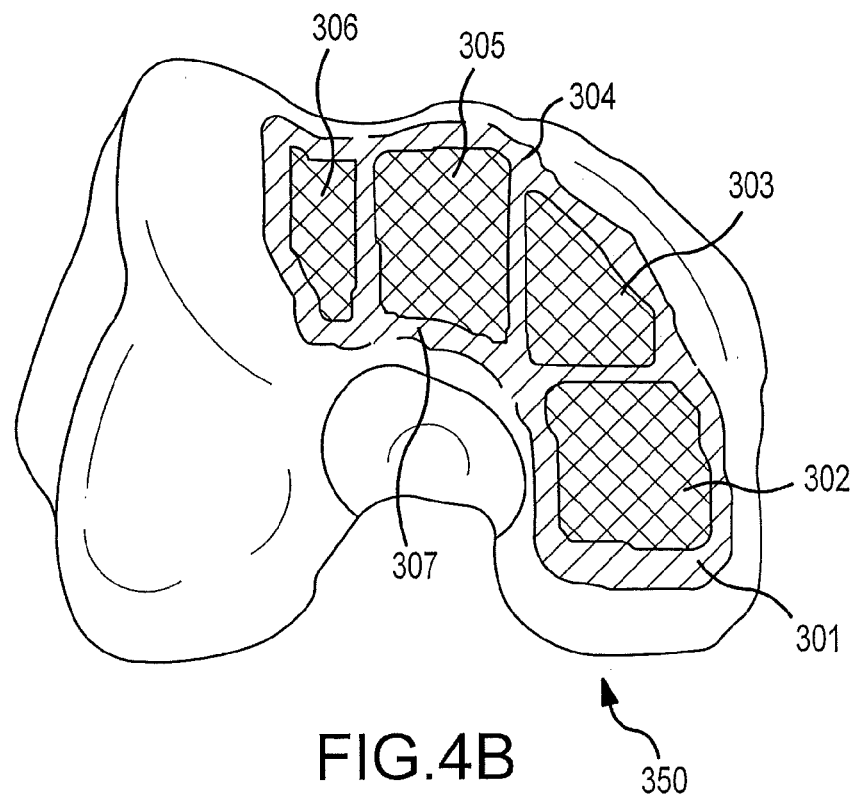
Figure 5A:
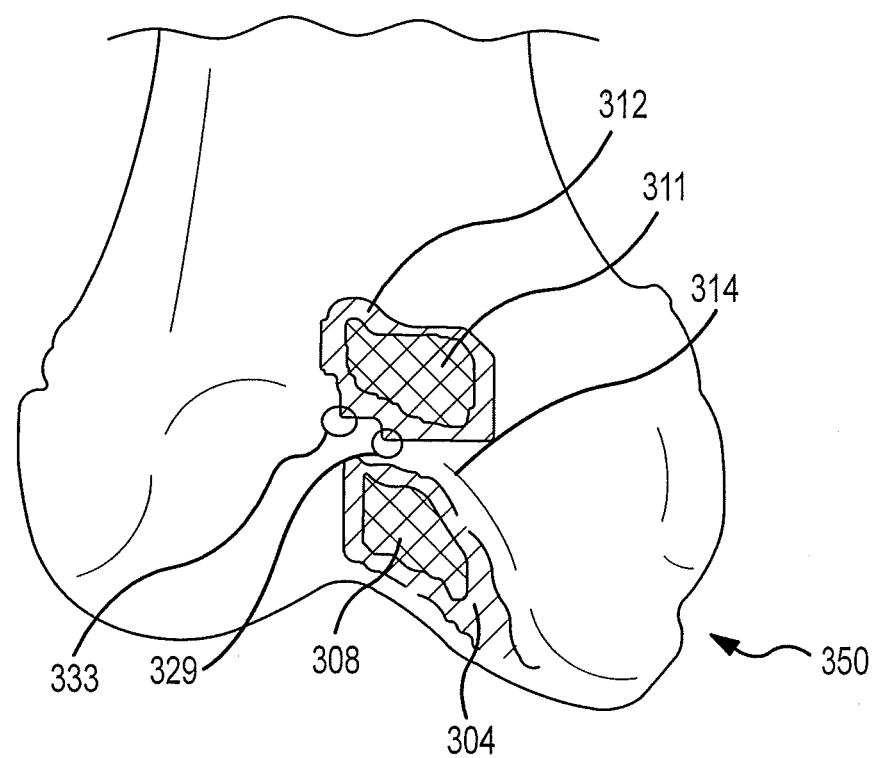
FIGS. 5A and 5B are, respectively, coronal and distal views of femoral condyles and displaying an embodiment having a reduced number of mating surfaces that still provides adequate stability of the uni-compartmental arthroplasty femur jig about the distal femoral condyle.
Figure 5B:
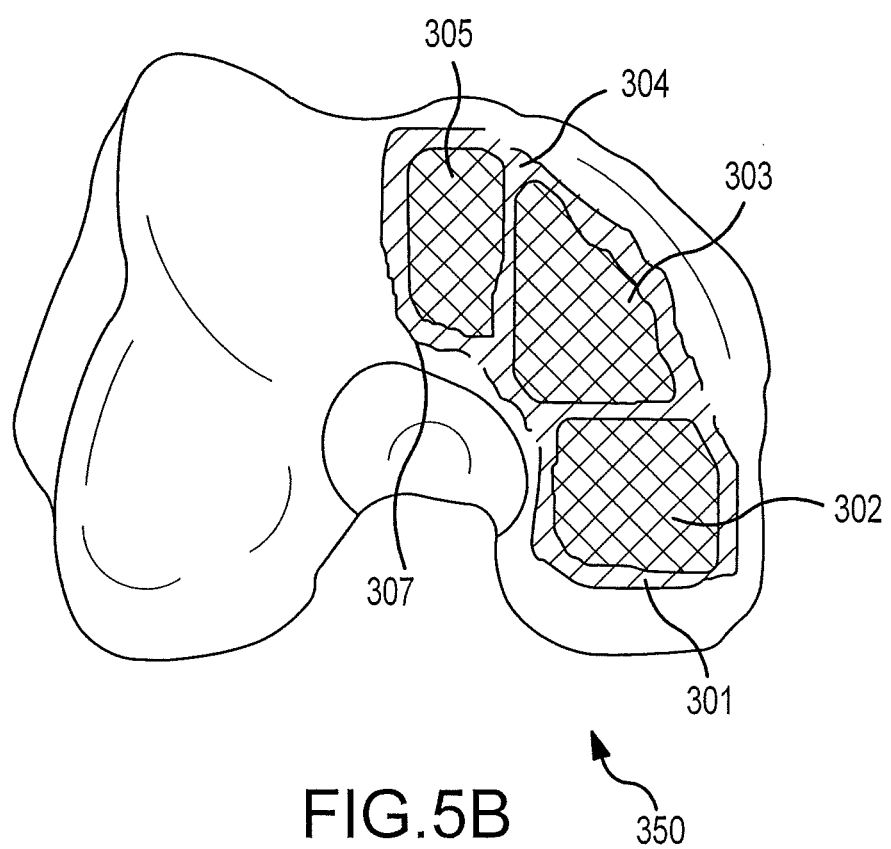

In one embodiment (FIGS. 4A and 4B), mating of the arthroplasty femur jig 2a occurs on the surfaces of the distal femur at the medial condyle 302, 303, the anterior cortex 310, 311, 313, into the trochlear groove 305, 306, 308, 309, and about the edge 314 of the anterior-proximal trochlear groove 307. In this embodiment, the combination of these surfaces serve as a condition that provides for reliable mating given the variety of patient bone anatomies. Specific mating surfaces are illustrated in FIGS. 4A and 4B with double cross-hatching illustrating discrete mating surfaces and single cross-hatching illustrating optional overall mating areas that may circumscribe or encompass the more discrete mating surfaces. These surfaces are defined as follows: the distal medial condyle 302, the anterior medial condyle 303, the medial anterior cortex 310, and the anterior cortex 311, 313, the distal medial trochlear groove 305, the antero-medial trochlear groove 308, and a portion 309 of the distal lateral trochlear groove and the antero-lateral trochlear groove that extends 5-6 mm lateral to the sulcus of the trochlear groove. The arthroplasty femur jig 2a may either mate to these surfaces specifically (as indicated by the double cross-hatching) or globally (as indicated by the single cross-hatching). For example, on the surfaces of the trochlear groove 307 and the medial condyle 301, the jig 2a could either mate to surfaces 302, 303, 305, 306, 308, 309 or globally to the area circumscribing these surfaces 304, which is illustrated with single cross-hatching. On the anterior cortex, the jig 2a could either mate to surfaces 310, 311, 313 or to the area circumscribing these areas 312.

As can be understood from FIG. 4A, the distal medial condyle 302 includes a distal semi-planar region of the articular surface of the medial condyle 301. The posterior edge of the distal medial condyle 302 begins where the articular surface of the medial condyle 301 begins to significantly curve towards a posterior region of the articular surface of the medial condyle 301, and the anterior edge of the distal medial condyle 302 begins where the articular surface of the medial condyle 301 begins to significantly curve towards the anterior medial condyle region 303 of the medial condyle 301.

The anterior medial condyle 303 includes an anterior region of the articular surface of the medial condyle 301. The posterior edge of the anterior medial condyle 303 begins where the articular surface of the medial condyle 301 begins to significantly curve towards the distal medial condyle 302 of the articular surface of the medial condyle 301, and the lateral edge of the anterior medial condyle 303 begins where the articular surface of the medial condyle 301 begins to significantly curve towards or transition into the medial region of the trochlear groove 307.

The distal medial trochlear groove 305 includes a distal-medial region of the articular surface of the trochlear groove 307. The medial edge of the distal medial trochlear groove 305 begins where the articular surface of the trochlear groove 307 begins to significantly curve or transition into the anterior medial condyle 303 of the articular surface of the medial condyle 301, and the lateral edge of the distal medial trochlear groove 305 begins where the articular surface of the trochlear groove 307 begins to curve out of or transition from the deepest portion of the trochlear groove 307.

The distal lateral trochlear groove 306 includes a distal-lateral region of the articular surface of the trochlear groove 307. The medial edge of the distal lateral trochlear groove 306 begins where the articular surface of the trochlear groove 307 begins to significantly curve or transition into the deepest portion of the trochlear groove 307, and the lateral edge of the distal lateral trochlear groove 306 begins where the articular surface of the trochlear groove 307 begins to curve or transition into the articular surface of the lateral condyle.

As can be understood from FIG. 4A, the antero-medial trochlear groove 308 includes an anterior-medial region of the articular surface of the trochlear groove 307. The antero-medial trochlear groove 308 is located between the anterior patellar facet boarder 314 and the distal medial trochlear groove 305. The lateral edge of the antero-medial trochlear groove 308 begins where the articular surface of the trochlear groove 307 begins to curve out of or transition from the deepest portion the of trochlear groove 307.

The antero-lateral trochlear groove 309 includes an anterior-lateral region of the articular surface of the trochlear groove 307. The antero-lateral trochlear groove 309 is located between the anterior patellar facet boarder 314 and the distal lateral trochlear groove 306. The lateral edge of the antero-lateral trochlear groove 309 begins where the articular surface of the trochlear groove 307 begins to curve or transition into the articular surface of the lateral condyle.

As indicated in FIG. 4A by the single cross-hatching, the overall anterior cortex or anterior optimal target region 312 is located on the anterior shaft of the femur proximal of the patellar facet boarder 314. The anterior optimal target region 312 may be generally coextensive with the generally planar surface area on the anterior shaft of the femur between the articularis genu 1000 and the patellar facet boarder 314. The region 312 may extend from a medial edge generally even with a line extending distally-proximally through the medial condyle to a lateral edge generally even with a line extending distally-proximally through the most lateral edge of the transition between the trochlear groove and the lateral condyle surface. The most distal edge of the region 312 may contact the patellar facet boarder 314 at discrete locations or points 329, 333. For example, a discrete point of contact with the patellar facet boarder 314 may be at a point 329 generally even with a line extending distally-proximally with the deepest portion of the trochlear groove. Another discrete point of contact with the patellar facet boarder 314 may be at a point 333 generally even with a line extending distally-proximally with a location half way through the transition between the trochlear groove and the lateral condyle surface.

As indicated in FIG. 4A by the double cross-hatching, multiple discrete target regions 310, 311, 313 may be identified within the overall anterior cortex or anterior optimal target region 312. Thus, although the anterior optimal target region 312 may be generally coextensive with the generally planar surface area on the anterior shaft of the femur between the articularis genu 1000 and the patellar facet boarder 314, the actual areas 310, 311, 313 within the anterior optimal target region 314 identified as being a reliable surface for the generation of the mating surfaces of arthroplasty jigs may be limited to any one or more of the areas 310, 311, 313. For example, an anterior-medial target region 310 forms a most medial discrete region within the overall region 312. The anterior-medial region 310 has a medial edge generally even with a line extending distally-proximally through the medial condyle, and a proximal edge generally even with a line extending distally-proximally through the transition between the medial condyle and the trochlear groove.

An anterior-center-medial target region 311 forms a central/medial discrete region within the overall region 312 just lateral of the region 310. The anterior-center-medial region 311 has a medial edge generally even with a line extending distally-proximally through the transition between the medial condyle and the trochlear groove, and a lateral edge generally even with a line extending distally-proximally through the deepest portion of the trochlear groove.

An anterior-lateral target region 313 forms a lateral discrete region within the overall region 312 just lateral of the region 311. The anterior-lateral region 313 has a medial edge generally even with a line extending distally-proximally through the deepest portion of the trochlear groove, and a lateral edge generally even with a line extending distally-proximally through the transition between the trochlear groove and the lateral condyle surface.

In another embodiment (FIGS. 5A and 5B), mating of the arthroplasty femur jig 2a occurs on the surfaces of the medial condyle 302, 303, 305, 308, the anterior-center-medial region 311, and about the anterior edge 314 of the anterior-proximal trochlear groove 307, each of these regions 302, 303, 305, 308 and 311 being substantially as described above with respect to FIGS. 4A-4B. This embodiment differs from that of FIGS. 4A and 4B in that the anterior shaft region 312 does not reach as far laterally or medially, and the medial condyle—trochlear groove region 304 the lateral portion of the trochlear groove. The method of mating for each of these embodiments is performed similarly and will be explained later.

For each of these embodiments, overestimating is performed at the rim 314 of articular cartilage, except at, for example, two points 329, 333 (FIG. 7), although in some embodiments it may be less than or greater than two points. "Hooking" occurs at the edge 314 of the anterior-proximal trochlear groove 307 instead of mating. "Hooking" is performed by matching, for example, two or more points 329, 333 to the rim of the articular cartilage as illustrated in FIG. 7, which shows a sliced section 330 of the femoral jig 2a where mating at the anterior surface occurs. Between hooking points 329, 333, the jig 2a is designed to overestimate the area, which is where there may be osteophytes or cartilage. The purpose of hooking to single points while overestimating other areas is to avoid mis-matching due to the unpredictable nature of osteophytes. In one embodiment, the anterior mating surface with hooking points incorporated is shown by the double cross-hatch section 328. As illustrated in FIG. 7, hooking occurs in a manner that steps down and hooks at another point. FIG. 10 illustrates this process during segmentation of the femur in the sagittal plane. In the active slice n, the segmentation line matches nearly precisely to the edge of the anterior-proximal trochlear groove. The segmentation line of slice n+1 is overestimated, while that of n−1 is nearly identical to the segmentation line of slice n. Between hooking points, at least one slice must be overestimated. The ideal edge to hook is illustrated in FIG. 10. The ideal edge protrudes from the anterior cortex at least 1 mm. Once segmentation is complete, the mating surface should resemble that of FIG. 7. For example, as shown in FIG. 6, hooking points 323, which correspond to points 329, 333 of the anterior-proximal edge of the trochlear groove, hook on points 329, 333.

A detailed discussion of the overestimation process is provided in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

Mating in the trochlear groove can be achieved with two different methods. In one method, mating 332 would be absolute as illustrated in FIG. 9. However, due to the drastic deflection at the trochlear groove of some femurs, absolute mating may not be reliable. For these cases, mating 331 may be done step-wise, as illustrated in FIG. 8. In this method, every other segmentation slice is matched precisely to the trochlear groove, while those in between are over-estimated. Segmentation is done in a similar manner to that described above and as illustrated for hooking in FIG. 10. To determine whether slices should be overestimated, segmentation in the trochlear groove may first be performed absolute with each slice matching the surface. Thereafter consecutive slices may be compared (slice n compared with slice n+1), if the distance between slices is greater than 1 mm, then the next slice (n+1) may be adjusted to reduce this distance, thereby overestimating the next slice (n+1). By overestimating this next slice (n+1), the following slice (n+2), can mate precisely to the trochlear groove without under-estimating the trochlear groove. Mating of the trochlear groove is generally performed as a combination of these methods.

As described above and can be understood from FIG. 6, the femur jig 2a may include a distal condylar mating region 316, trochlear groove mating region 320 and an anterior cortex mating region 326. The mating regions or surfaces 316, 320, 326 of the arthroplasty femur jig 2a that correspond and mate specifically to the surfaces defined above with respect to FIGS. 4A-5B are illustrated in FIG. 6. In general, surface 315 mates to the distal medial condyle 302, surface 317 mates to the anterior medial condyle 303, surface 318 mates to the distal medial trochlear groove 305, surface 321 mates to the antero-medial trochlear groove 308, surface 319 mates to the distal lateral trochlear groove 306, surface 322 mates to the antero-lateral trochlear groove 309, surface 327 mates to the medial anterior cortex 310, surfaces 325 and 324 mate to the anterior cortex 311 and 313, respectively, and points 323 hook onto the edge 314 of the anterior-proximal trochlear groove 307 at points 329, 333.

As can be understood from the proceeding discussion regarding the mating contact surfaces (indicated by single and double cross hatch regions in FIGS. 4A-4B and 5A-5B) of the distal femur and the corresponding mating contact surfaces (indicated by single and double cross hatch regions in FIG. 6) of the inner side of the uni-compartmental arthroplasty jig, the inner side of the jig matingly receives the arthroplasty target region of the distal femur as shown in FIG. 2A. However, although the inner side of the femoral jig matingly receives the arthroplasty target region of the distal femur, only those mating contact regions (indicated by single and double cross hatch regions in FIG. 6) of the inner side of the jig actually make mating contact with the mating contact regions (indicated by single and double cross hatch regions in FIGS. 4A-4B and 5A-5B) of the distal femur. All other regions (those regions not single or double cross hatched in FIG. 6) of the inner side of the jig do not make contact with corresponding surfaces of the distal femur on account of being defined according to the overestimation process. Thus, in one embodiment, the double cross hatch regions of the inner side of the jig and the distal femur may be the only regions that make mating contact because the rest of the inner side of the jig is the result of the overestimation process. In another embodiment, both the single and double cross hatch regions of the inner side of the jig and the distal femur may be the only regions that make mating contact because the rest of the inner side of the jig is the result of the overestimation process. Regardless, the inner side of the jig is configured to matingly receive the distal femur such that the jig has a customized mating contact with the distal femur that causes the jig to accurately and securely sit on the distal femur in a stable fashion such that the jig may allow the physician to make the distal cut with an accuracy that allows the femoral implant to restore the patient's joint to its pre-degenerated or natural alignment state. This accurate and stable customized mating between the jig and femur is facilitated by the jig mating contact regions being based on regions of the femur that are accurately identified and reproduced from the medical imaging (e.g., MRI, CT, etc.) used to generate the various bone models, and overestimating in those regions that are not accurately identified and reproduced due to issues with the medical imaging and/or the inability to machine the identified bone features into the inner side of the jig.

Figure 11A:
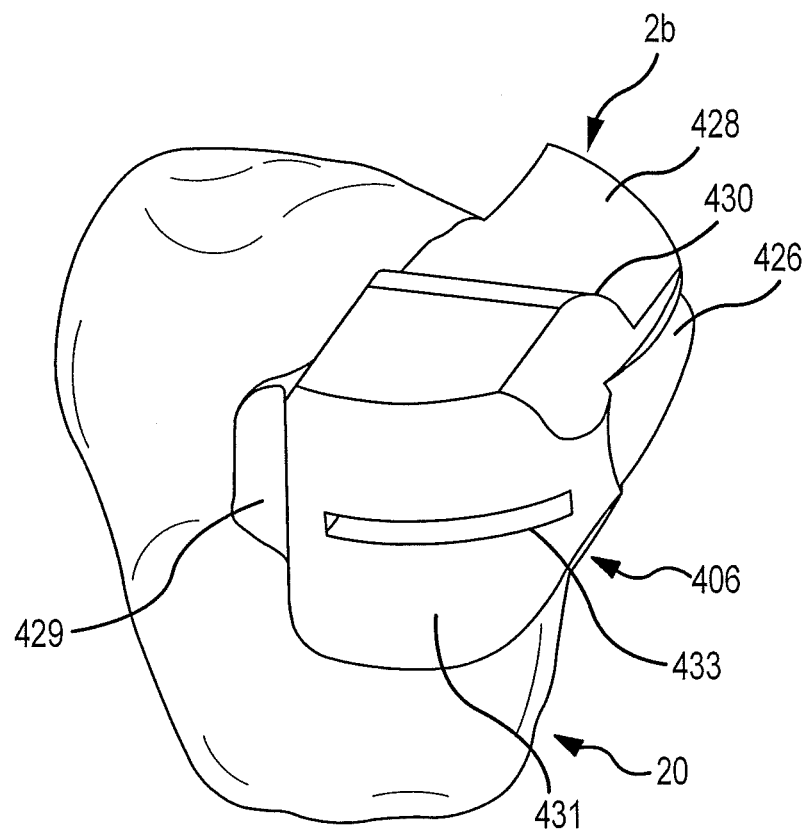
FIG. 11A is an isometric view of a uni-compartmental tibial arthroplasty jig that may be produced by the methods disclosed herein in a customized state, wherein the jig is shown on the proximal tibia.
Figure 11B:
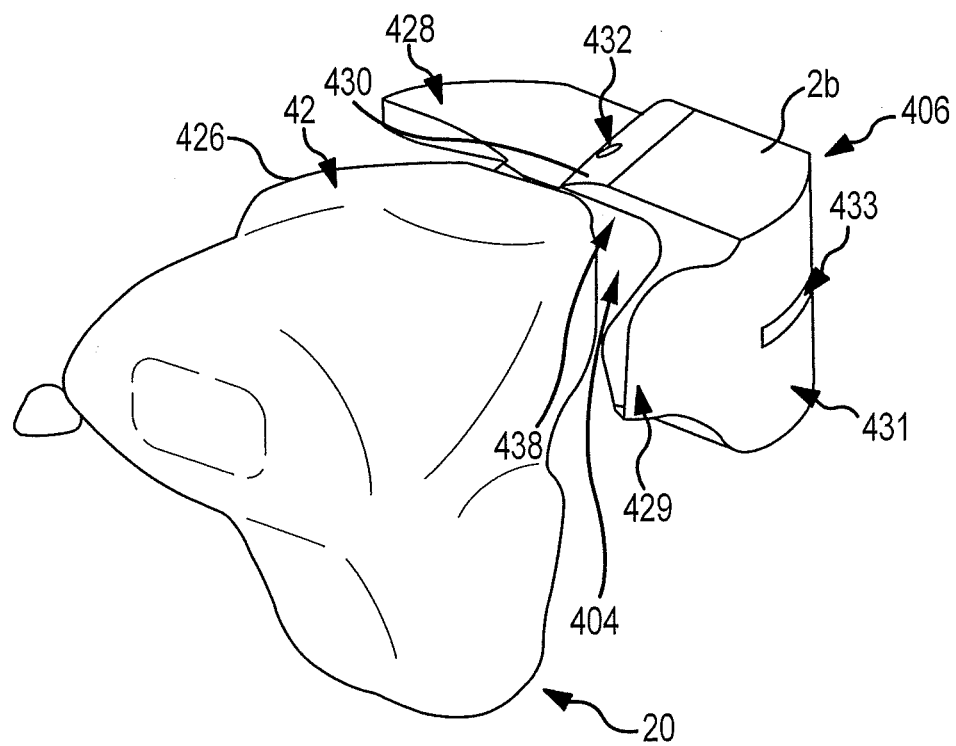
FIG. 11B is the tibial arthroplasty jig of FIG. 11B, except the jig is shown off the proximal tibia.
Figure 11C:
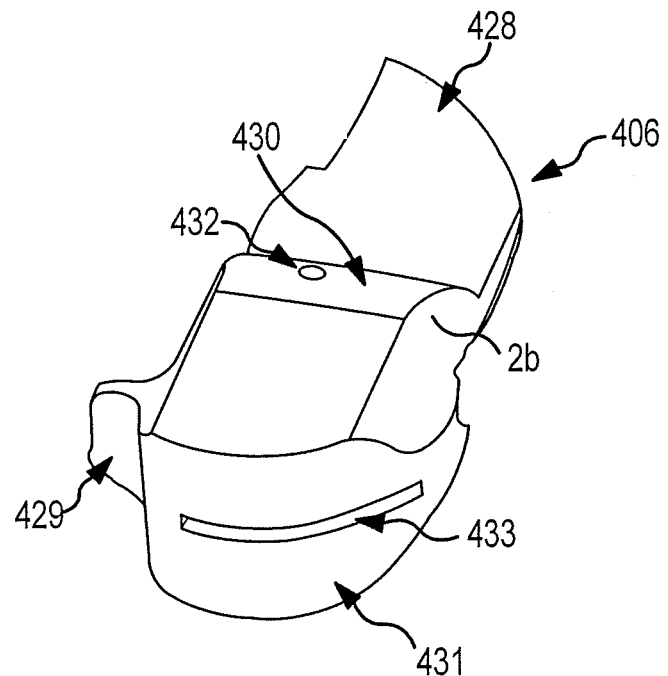
FIG. 11C depicts a top view of the uni-compartmental tibial arthroplasty jig, wherein the tibia is not shown.
Figure 11D:
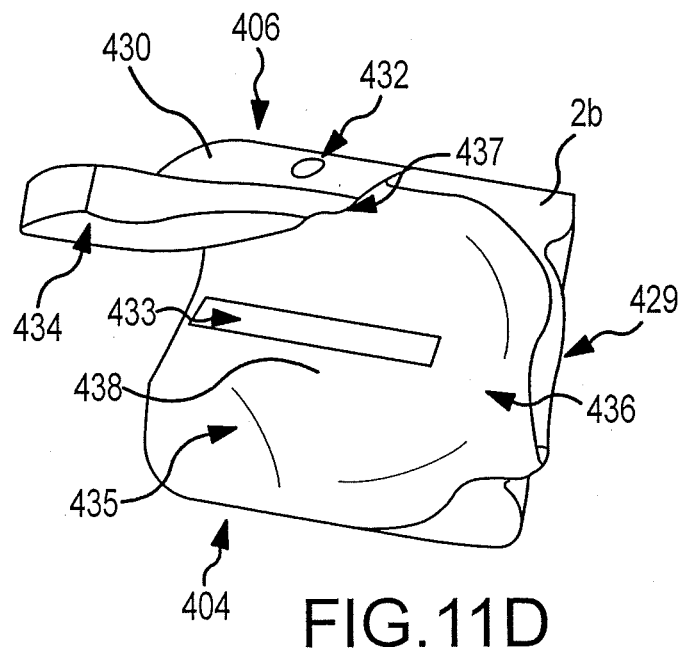
FIG. 11D depicts a bottom view of the uni-compartmental tibial arthroplasty jig of FIG. 11C.
Figure 11E:
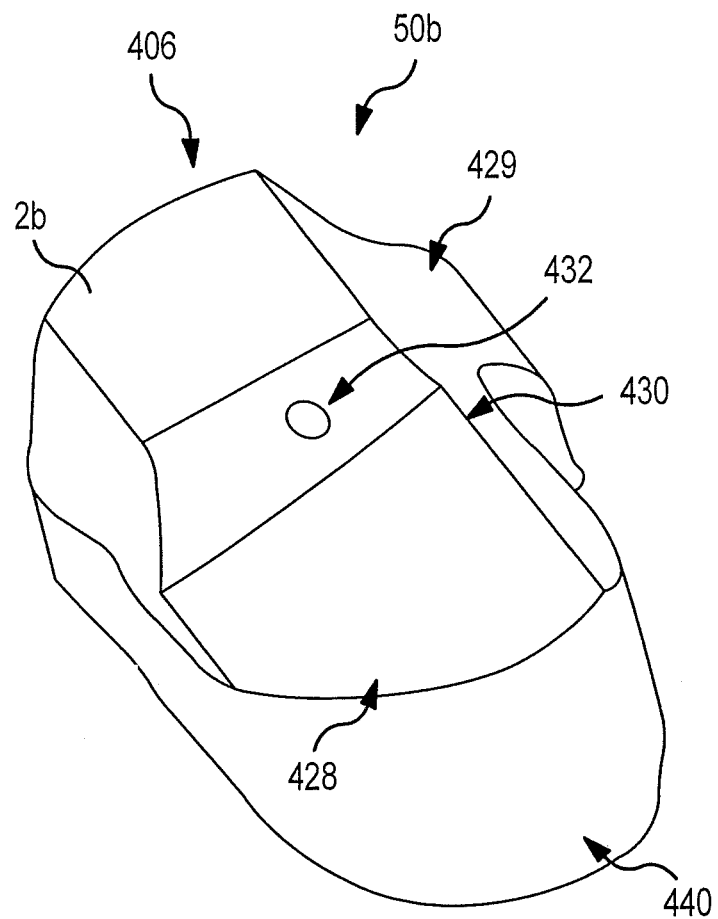
FIG. 11E depicts a top view of the uni-compartmental tibial arthroplasty jig of FIG. 11C, except the jig is in a non-customized state.

For a discussion of the tibia arthroplasty jig 2b, reference is first made to FIGS. 11A-11E. FIGS. 11A-11B are isometric views of the tibial arthroplasty jig 2b in a customized state, wherein the jig is shown on (FIG. 11A) or off (FIG. 11B) the proximal tibia 20. FIGS. 11C-11E depict top and bottom views of the tibial arthroplasty jig 2b in a customized state, wherein the tibia is not shown. FIG. 11E shows a top view of the jig 2b of FIG. 11C, wherein the jig 2b is in a non-customized state (e.g., the jig 2b is in the form of a jig blank 50b from which the jig 2b is created machining or other manufacturing methods).

As indicated in FIGS. 11A-11E, a tibia arthroplasty jig 2b may include an interior side or portion 404 and an exterior side or portion 406. When the tibia cutting jig 2b is used in a UKA procedure, the target area 438 of the interior side or portion 404 faces and matingly receives the arthroplasty target area 42 of the tibia proximal end, and the exterior side or portion 406 is on the opposite side of the tibia cutting jig 2b from the interior portion 404.

As may be best understood with reference to FIG. 11D, the interior portion 404 of the tibia cutting jig 2b may include a horizontal cut clot 433, a proximal drill hole 432, a target area 438, and mating portions 434, 435, 436, 437. The interior portion 404 of the tibia jig 2b is configured to match the surface features of the damaged proximal end (i.e., the arthroplasty target area 42) of the patient's tibia 20. Thus, when the target area 42 is received in the interior portion 404 of the tibia jig 2B during the UKA surgery, the surfaces of the target area 42 and interior portion 404 matingly match.

The surface of the interior portion 404 of the tibia cutting jig 2b is machined or otherwise formed into a selected tibia jig blank 50B and is based or defined off of a 3D surface model 40 of a target area 42 of the damaged upper end or target area 42 of the patient's tibia 20.

As indicated in FIGS. 11A-11C and 11E, the exterior portion 406 of the tibial jig 2b may include a medial plateau portion 428, an anterior cortex flange 429, a medial anterior cortex portion 431, a medial tibial upslope portion 430, a horizontal cut clot 433, a proximal drill hole 432, and finally a target area 438. As can be understood from FIG. 11E, in a non-customized state, the jig 2b may include a customizable portion 440 which may be customized to help properly position the jig 2b during surgery. Thus, together with the features of the interior portion 404 of the jig 2b, the exterior portion 406 helps the jig 2b to mate stably with the medial tibia 426 and position a drill hole 432 and horizontal cut slot 433. With this drill hole and horizontal cut slot, the proximal/distal, internal/external, varus/valgus positions of the uni-condylar tibial implant may be set.

Figure 12A:
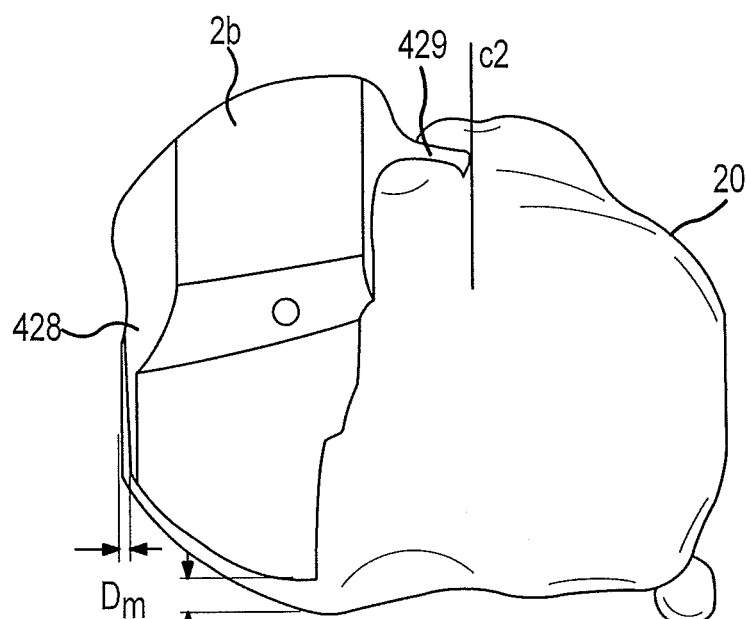
FIG. 12A illustrates the length of the tibial plateau that one embodiment of the tibial jig may cover.
Figure 12B:
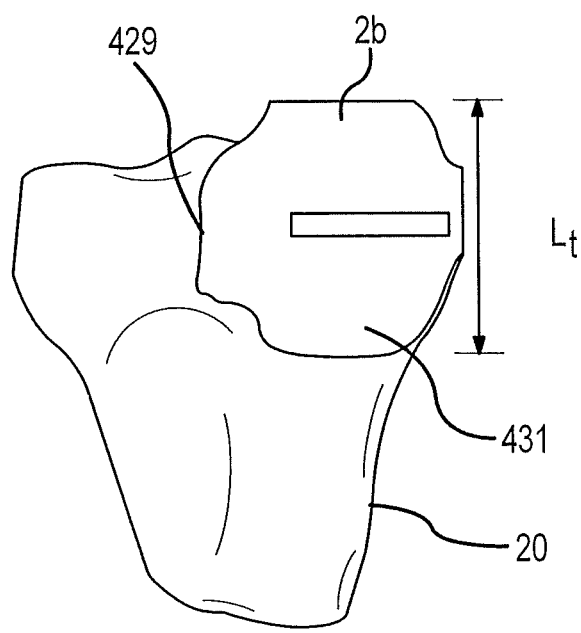
FIG. 12B illustrates the height of one embodiment of the tibial jig.

For a discussion of certain sizing measurements that may be utilized in the development of the tibial cutting jig 2b, reference is now made to FIGS. 12A-12B. FIG. 12A illustrates the coverage of the tibial plateau that one embodiment of the tibial jig 2b may cover. FIG. 12B illustrates the height of one embodiment of the tibial jig 2b.

The size of the tibial jig 2b is determined by the size of the patient's bone 20. FIG. 12A illustrates the parameters which determine how much of the tibial plateau the jig 2b should cover. In one embodiment, the medial edge of the tibial plateau portion 428 of the tibial jig 2b has a distance $D_m$ of approximately 1-2 mm from the medial edge of the tibial plateau. Also, the posterior edge of the tibial plateau portion 428 of the tibial jig 2b has a distance $D_p$ of approximately 3-5 mm from the posterior edge of the tibial plateau. In one embodiment as depicted in FIG. 12A, the anterior cortex flange 429 should not reach further than midway past the patellar insertion as illustrated by line c2. In one embodiment as shown in FIG. 12B, the length $L_t$ the jig 2b between the top surface of the jig 2b and the bottom edge of the medial anterior cortex portion 431 is approximately 40 mm. The horizontal cut slot 433 should be positioned at the level which the proximal/distal and varus/valgus positions of the unicondylar tibial implant should be set.

Figure 13A:
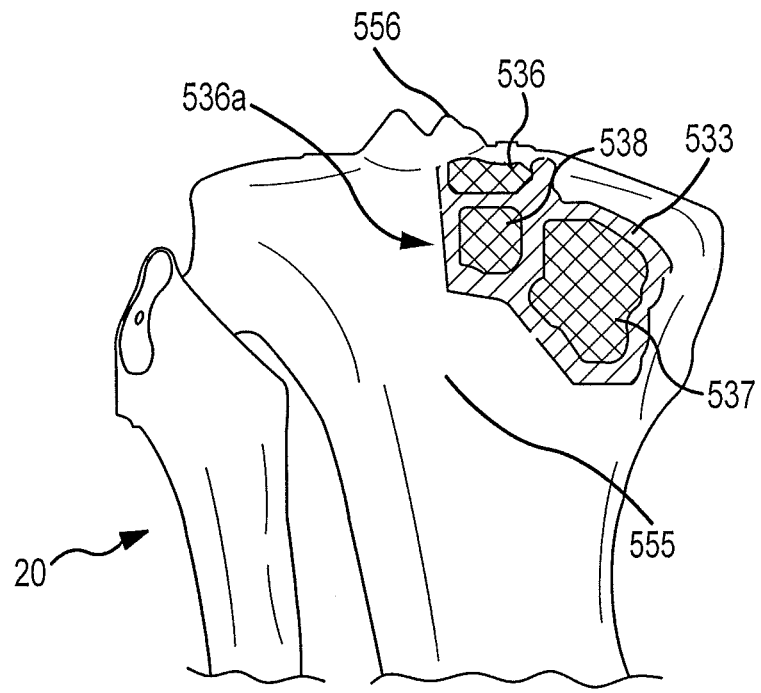
FIGS. 13A and 13B are, respectively, an anterior coronal view and a proximal axial view of one embodiment of the mating surfaces for the tibial arthroplasty jig on the proximal tibia.
Figure 13B:
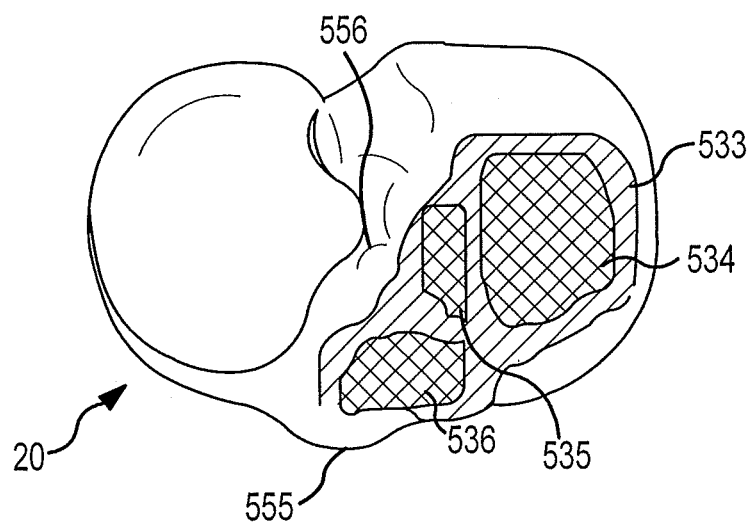
Figure 14A:
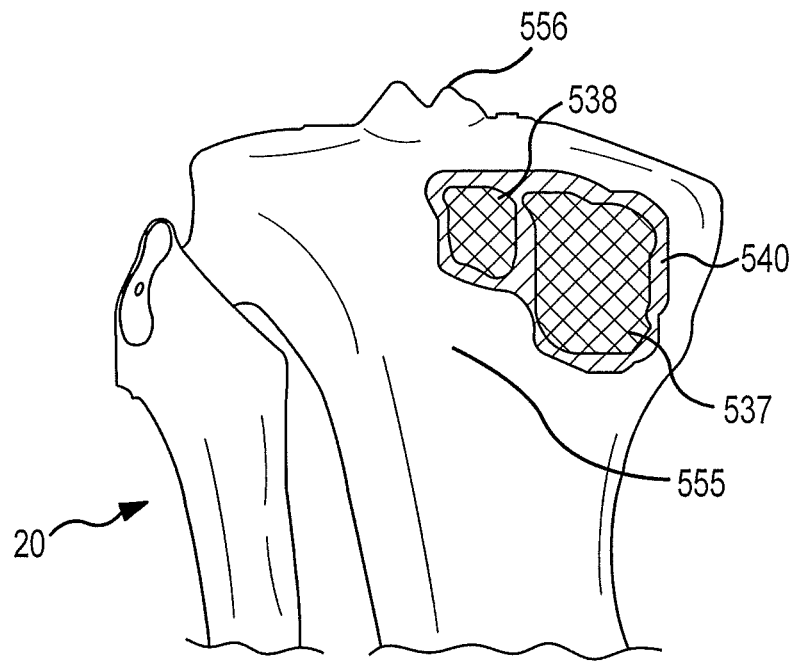
FIGS. 14A-14B are, respectively, an anterior coronal view and a proximal axial view of a second embodiment of the mating surfaces for the tibial arthroplasty jig on the proximal tibia.
Figure 14B:
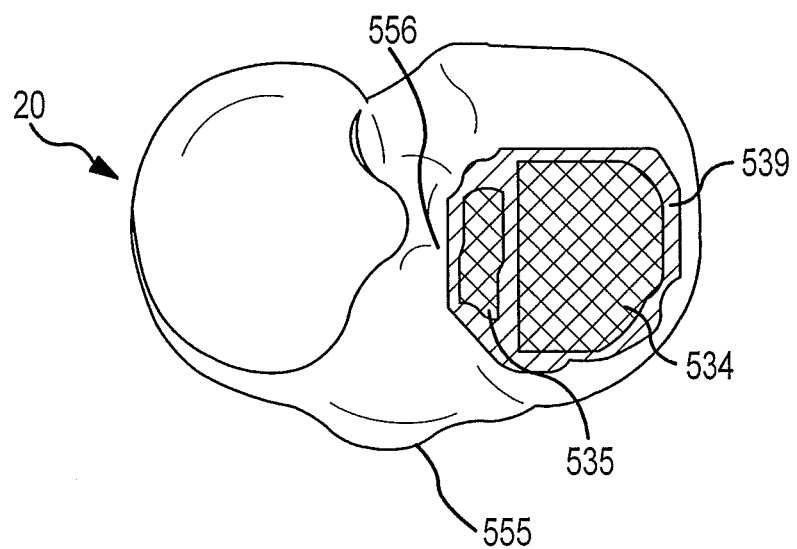
Figure 15:
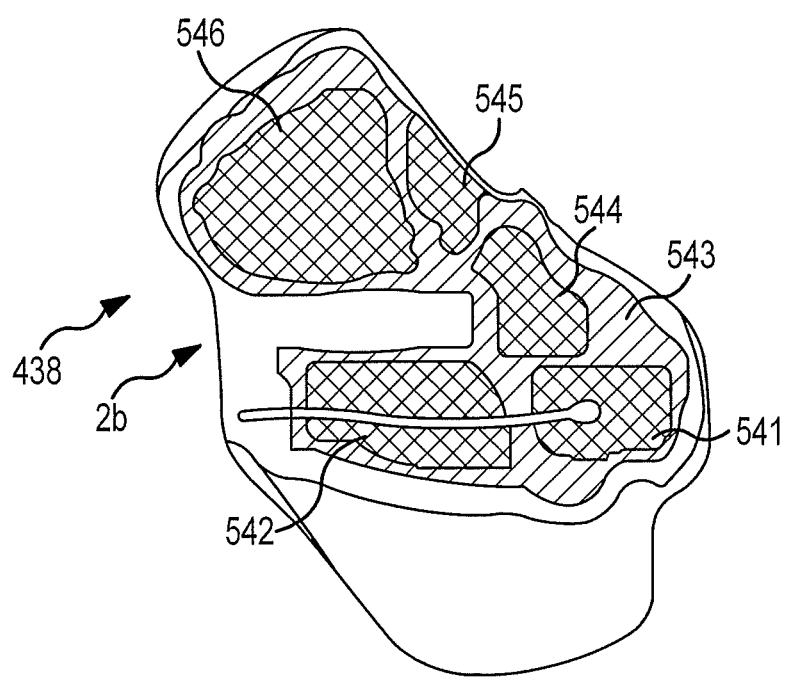
FIG. 15 illustrates the uni-compartmental tibial arthroplasty jig with mating surfaces corresponding to those of the proximal tibia depicted in FIGS. 13A-13B.
Figure 16:
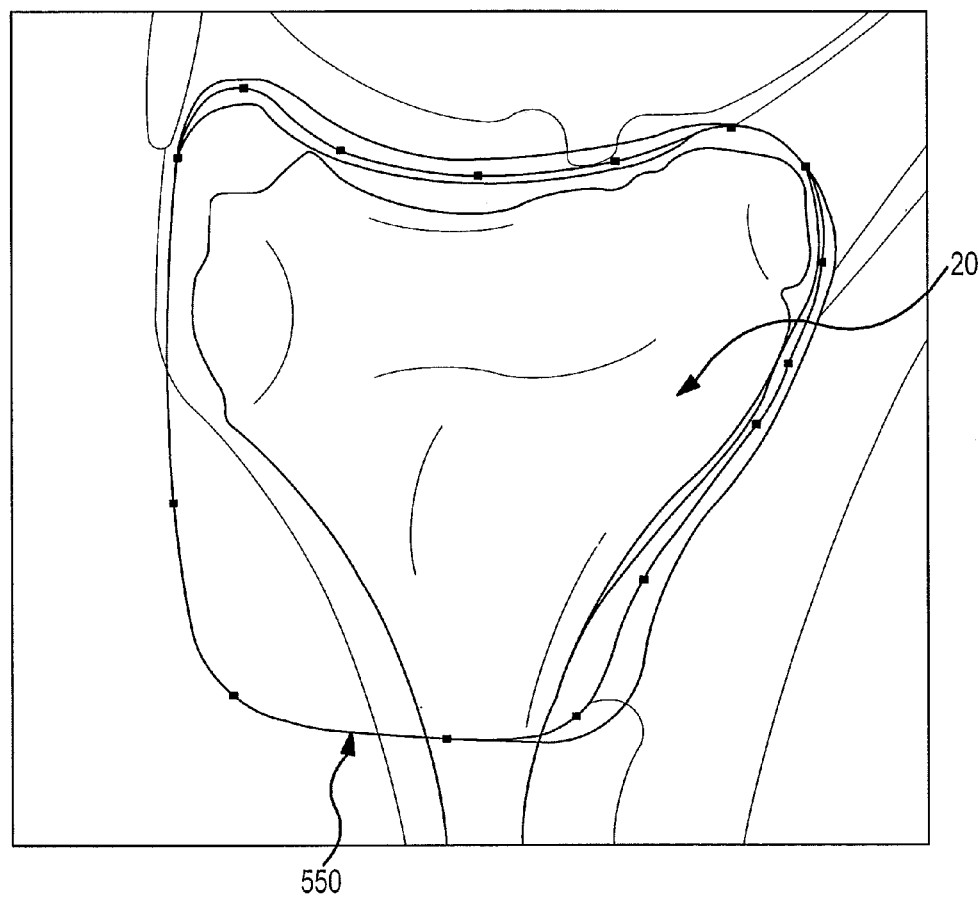
FIG. 16 is a single MRI slice in the sagittal plane at the medial upslope of the intercondyloid eminence.

For a discussion of the mating surfaces for the tibial arthroplasty jig 2b, reference is now made to FIGS. 13A-18B. FIGS. 13A and 13B are, respectively, an anterior coronal view and a proximal axial view of one embodiment of the mating surfaces for the tibial arthroplasty jig 2b on the proximal tibia 20. FIGS. 14A-14B are, respectively, an anterior coronal view and a proximal axial view of a second embodiment of the mating surfaces for the tibial arthroplasty jig 2b on the proximal tibia 20. FIG. 15 illustrates the tibial arthroplasty jig 2b with mating surfaces corresponding to those of the proximal tibia depicted in FIGS. 13A-13B. FIG. 16 is a single MRI slice in the sagittal plane at the medial upslope of the intercondyloid eminence. FIGS. 17A-18B illustrate various methods of the tibial arthroplasty jig 2b mating with the medial upslope 602 of the intercondyloid eminence 600.

The tibial arthroplasty jig 2b mates to the medial surfaces of the proximal tibia 20. In one embodiment, for stability, the guide 2b may at least mate to the surfaces that are illustrated in FIG. 13A-13B. FIGS. 14A-14B illustrates another embodiment of the mating conditions that lead to stability. Both of these embodiments incorporate some or all of the areas illustrated by the double cross hatch markings 534, 535, 536, 537 and 538 in FIGS. 13A-14B. These areas are: the medial tibial plateau 534, the medial anterior tibial cortex 537, the anterior cortex 538 superior to the tuberosity 555, the medial upslope 535 of the intercondyloid eminence 556, and a region 536 extending from anterior the intercondyloid eminence 556 to towards the tuberosity 555 over the edge transition from the tibial plateau region (FIG. 13A) to the tibial anterior region (FIG. 13B). In one embodiment, the tibial arthroplasty jig 2b may include mating surfaces that matingly engage some or all of these discrete areas 534, 535, 536, 537, 538 or mating surfaces of the jig 2b may matingly engage more globally the discrete mating surfaces 534, 535, 536, 537, 538 and the surrounding areas 533, 539, 549 as illustrated with the single hatch markings in FIGS. 13A-14B. Specifically, the jig 2a may have mating surfaces that matingly engage the region of the tibia encompassed by the single hatch area 539 on the tibial plateau and single hatch area 540 on the anterior region of the proximal tibia, as reflected in FIGS. 14A-14B, or the single hatch area 533 which extends over the tibial plateau and anterior region of the proximal tibia, as illustrated in FIGS. 13A-13B.

As shown in FIGS. 13A and 13B by the cross-hatching, the optimal target region 533 on the anterior side of the tibial shaft may be divided into two sub-regions 537 and 538. The first or medial sub-region 537 may be a generally planar surface region that extends distally from generally the plateau edge or capsule line to a point generally even with the beginning of the distal half to distal third of the tibial tuberosity 555. The sub-region 537 may extend medial-lateral from the medial edge of the medial tibia condyle to a point generally even with a medial edge of the tibial tuberosity 555.

The center sub-region 538 may be a generally planar surface region that extends distally from generally the plateau edge or capsule line to a point near the proximal boundary of the tibial tuberosity 555. The center sub-region 538 may extend medial-lateral from the lateral edge of the medial sub-region 537 to a point generally even with a center of the tibial tuberosity 555 or even to the lateral edge of the tibial tuberosity 555.

To result in a jig 2a having mating surfaces that only matingly engage or contact some or all of the above-discussed surfaces of the tibia 20, overestimation during the segmentation process may be employed to over-machine those areas of the jig 2a that correspond to those surfaces of the tibia 20 that are outside the double cross hatched regions and/or the single cross hatched regions depicted in FIGS. 13A-14B. The result of such an overestimation process is a jig 2a does not make contact with those regions of the tibia 20 that are outside the double and/or single cross hatch regions of the tibia 20, the jig 2a only making mating, secure and stable contact with the double cross hatch, single cross hatch, combinations thereof, or portions thereof.

In the other embodiment as illustrated in FIGS. 13A and 13B, one additional mating area 536 may be the ridge superior to the tuberosity and anterior to the intercondyloid eminence 556 where insertion of the ACL takes place. At this ridge there may be irregular osteophytes as shown in FIG. 16. Mating in this area may help to stabilize internal/external rotation. Because of the irregularity of osteophytes in this region, mating here may not be absolute. Segmentation may "hug" this region as shown in FIG. 16. Between slices, segmentation may take care to over-estimate in order not to segment too closely and cause rocking of the jig.

Figures 17A, 17B:
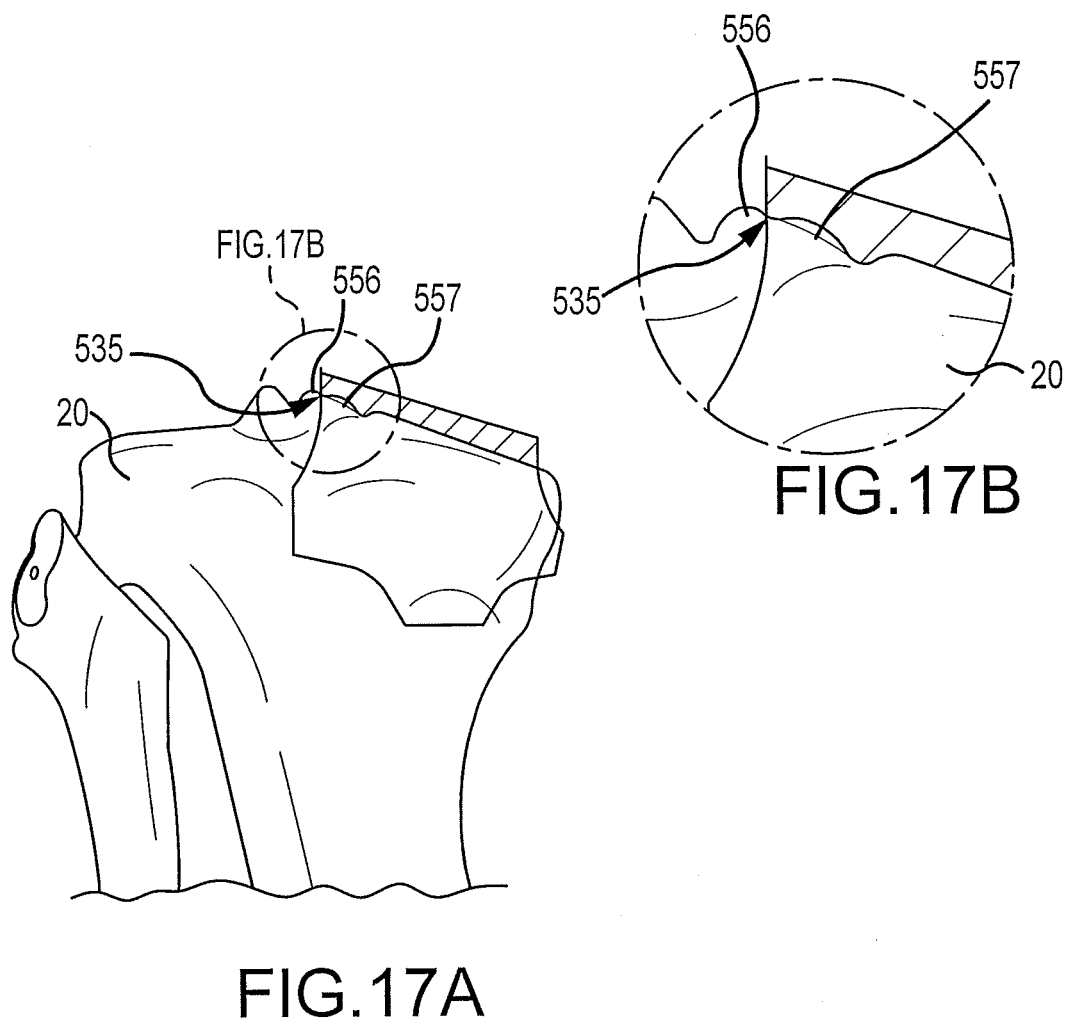
FIG. 17A illustrates one method of the uni-compartmental tibial arthroplasty jig mating with the medial upslope of the intercondyloid eminence.
FIG. 17B is an enlarged view of FIG. 17A.
Figures 18A, 18B:
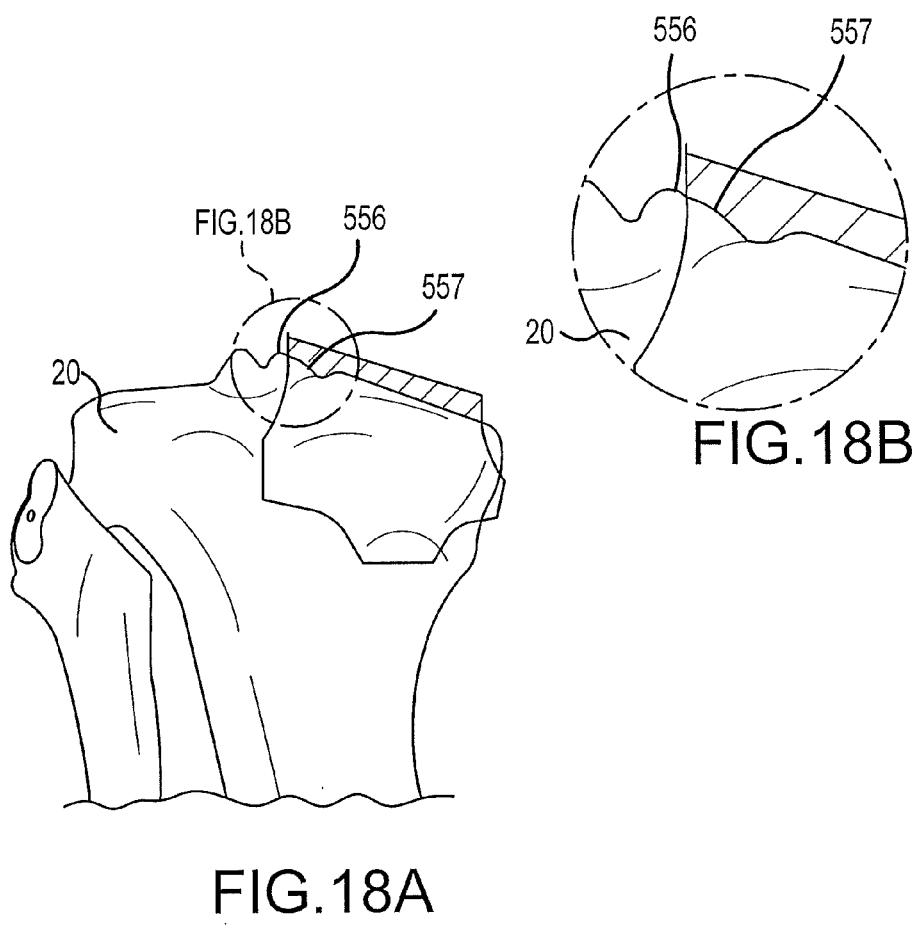
FIG. 18A illustrates another method of the uni-compartmental tibial arthroplasty jig mating with the medial upslope of the intercondyloid eminence.
FIG. 18B is an enlarged view of FIG. 18A.

In some embodiments, mating at the medial upslope 535 of the intercondyloid eminence 556 may be necessary to stabilize internal/external rotation. Because of the rapid change in geometry at the up slope, to facilitate accurate mating at this location 535, overestimation may be performed to prevent mismatching. FIGS. 17A-18B illustrate two methods of mating to the medial upslope 557 of the intercondyloid eminence 556. FIGS. 17B and 18B illustrate an enlarged view of the upslope 557 in a coronal plane. In one method as depicted in FIG. 18B, mating may be absolute and sequential segmentation lines in the sagittal plane may be drawn to mate precisely to the cartilage surface of the upslope 557 of the intercondyloid eminence 556. Since segmentation slices in the sagittal plane are drawn 2 mm apart from one another, interpolation between slices may not represent the geometry of the upslope. This first method may be performed if in checking sequential slices, the distance between slices is not greater than 1 mm. Otherwise, the method illustrated in FIGS. 17A-17B may be performed to segment the upslope of the tibial spine. In one embodiment of this method, at least one segmentation slice 550 (see FIG. 16) in the sagittal plane should mate precisely to the medial upslope of the intercondyloid eminence. Slices between this mating slice and those slices that mate to the medial plateau may be overestimated. As a result, the upslope mating region 535 may be as indicated in FIG. 17B, the rest of the upslope 557 being overestimated so no other contact between the jig 2a and upslope 557 occurs, other than at region 535 (compare FIG. 18B at 557 for example of no overestimation and FIG. 17B at 557 for example of overestimation).

As can be understood from FIGS. 13A and 13B, the proximal tibia 20 includes a general mating area 533 that extends over or incorporates areas 536, 537, 538 of the tibial anterior region near the tibial plateau (FIG. 13A) and areas 534, 535, 536 of the tibial plateau itself (FIG. 13B), the general mating area 533 being identified in FIGS. 13A and 13B via a single cross hatch and including the double hatch regions 534, 535, 536, 537, 538 encompassed by the single cross hatch. As illustrated in FIGS. 14A and 14B, in another embodiment, a general mating area extends over areas 534, 535 of the medial tibial plateau 539 (FIG. 14B), and a general mating area over areas 537, 538 of the medial anterior cortex 540 (FIG. 14A), each of the regions 539, 540 being identified by single cross-hatch markings and including the double hatch regions 534, 535, 537, 538 encompassed by the single cross hatch.

As can be understood from FIG. 15, the tibial jig 2b includes a general mating area 543 (FIG. 15), which is identified by single cross-hatch markings and defined in the inner surface 438 of the jig 2b (see FIGS. 11B and 11D). The surfaces within the target area 438 of the tibial arthroplasty jig 2b that mate to corresponding surfaces of the tibia 20 are illustrated by the double cross hatch markings in FIG. 15. Areas that are outside the single cross hatch markings 543 may not mate with the corresponding surfaces of the proximal tibia and are overestimated. Specifically, the corresponding surfaces within the tibial arthroplasty jig 2b target area 438 that mate with the proximal tibia 20 are the following: surface 546 matingly contacts the medial plateau 534, surface 545 matingly contacts the medial upslope 535 of the intercondyloid eminence 556, surface 544 matingly contacts the region 536 that incorporates the ridge superior to the tuberosity 555 and anterior to the intercondyloid eminence 556, surface 541 matingly contacts the anterior cortex 538 superior to the tuberosity 555, and surface 542 matingly contacts the medial anterior cortex 537. The single cross hatch region 543 of the mating target region 438 of the jig 2b may, depending on the embodiment, be configured to matingly contact the single cross hatch regions 533, 539, 540 shown in FIGS. 13A-14B. Alternatively, if the image slices are not sufficiently narrow or the topography of the tibia 20 does not lend itself to accurate mating replication for the jig 2a, the regions 533, 539, 540 may be near, but slightly offset from the corresponding surfaces 533, 539, 540 of the tibia 20 due to overestimation, the regions 541, 542, 544, 545 and 546 being the only portions of the jig 2a that actually matingly contact the corresponding regions 534, 535, 536, 537 and 538 of the tibia 20.

As can be understood from the proceeding discussion regarding the mating contact surfaces (indicated by single and double cross hatch regions in FIGS. 13A-14B) of the proximal tibia 20 and the corresponding mating contact surfaces (indicated by single and double cross hatch regions in FIG. 15) of the inner side 438 of the uni-compartmental arthroplasty jig 2b, the inner side 438 of the jig 2b matingly receives the arthroplasty target region 42 of the proximal tibia 2b as shown in FIG. 11A. However, although the inner side 438 of the tibia jig 2b matingly receives the arthroplasty target region 42 of the proximal tibia 20, only those mating contact regions (indicated by single and double cross hatch regions in FIG. 15) of the inner side of the jig actually make mating contact with the mating contact regions (indicated by single and double cross hatch regions in FIGS. 13A-14B) of the proximal tibia. All other regions (those regions not single or double cross hatched in FIG. 15) of the inner side of the jig do not make contact with corresponding surfaces of the proximal tibia on account of being defined according to the overestimation process. Thus, in one embodiment, the double cross hatch regions of the inner side of the jig and the proximal tibia may be the only regions that make mating contact because the rest of the inner side of the jig is the result of the overestimation process. In another embodiment, both the single and double cross hatch regions of the inner side of the jig and the proximal tibia may be the only regions that make mating contact because the rest of the inner side of the jig is the result of the overestimation process. Regardless, the inner side of the jig is configured to matingly receive the proximal tibia such that the jig has a customized mating contact with the proximal tibia that causes the jig to accurately and securely sit on the proximal tibia in a stable fashion such that the jig may allow the physician to make the proximal cut with an accuracy that allows the tibia implant to restore the patient's joint to its pre-degenerated or natural alignment state. This accurate and stable customized mating between the jig and tibia is facilitated by the jig mating contact regions being based on regions of the tibia that are accurately identified and reproduced from the medical imaging (e.g., MRI, CT, etc.) used to generate the various bone models, and overestimating in those regions that are not accurately identified and reproduced due to issues with the medical imaging and/or the inability to machine or otherwise manufacture the identified bone features into the inner side of the jig.

The discussion provided herein is given in the context of uni-compartmental jigs and the generation thereof. However, the disclosure provided herein is readily applicable to total arthroplasty procedures in the knee or other joint contexts. Thus, the disclosure provided herein should be considered as encompassing jigs and the generation thereof for both total and uni-compartmental arthroplasty procedures. Additionally, while the discussion is given in the context of restoring the patient to their natural alignment, the concepts taught herein are also readily applicable to arthroplasty procedures causing the patient's knee to be zero mechanical axis. Thus, the disclosure contained herein should be considered to encompass both natural alignment and mechanical axis alignment. Additionally, the discussion provided herein is given in the context of medial uni-compartmental knee jigs but the teachings are equally applicable to lateral uni-compartmental knee jigs; therefore the disclosure should be considered to encompass both medial and lateral uni-compartmental knee jigs.

Figure 19:
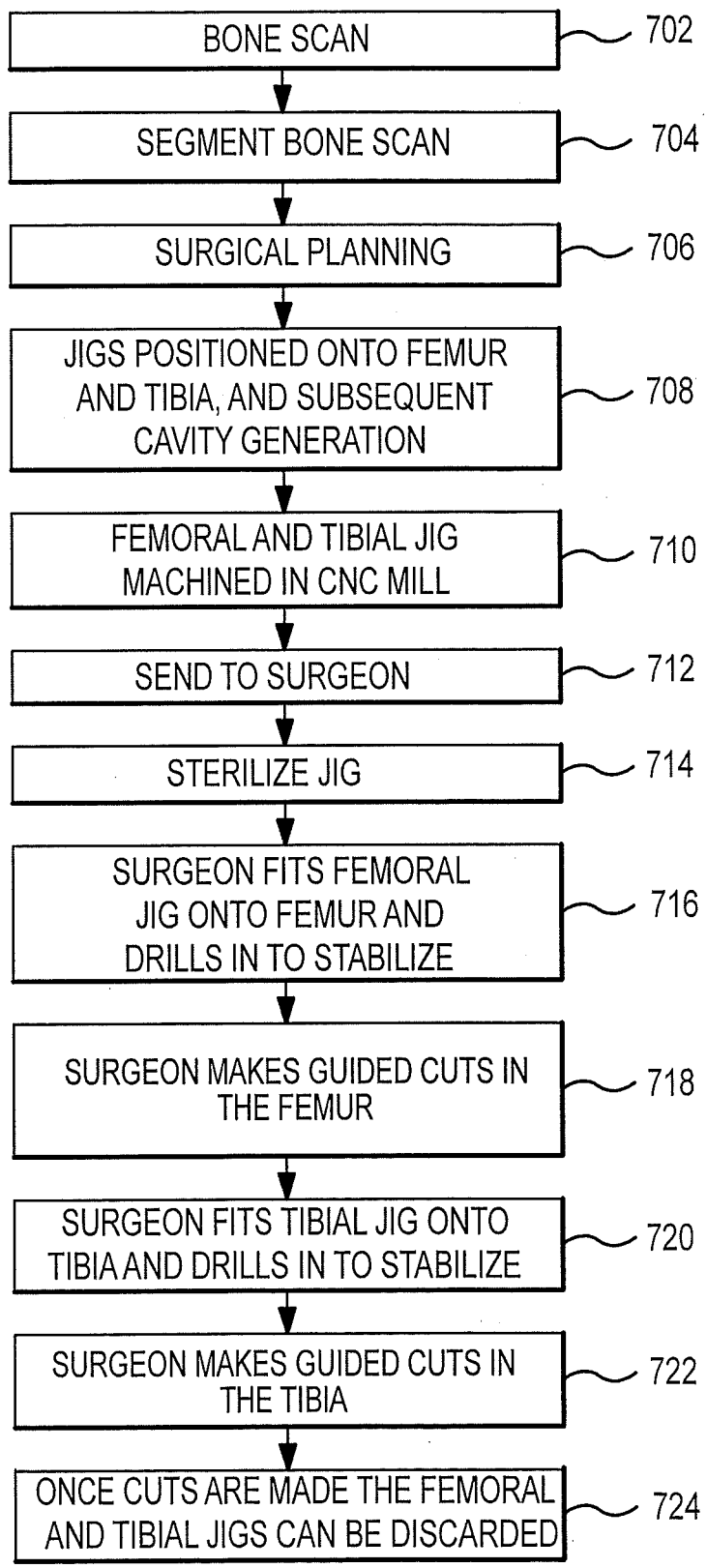
FIG. 19 is a flow chart outlining production to use of the arthroplasty jigs of FIGS. 2A and 11A.

For an overview of an embodiment of the above-described methods of design, manufacture and use of the above-described arthroplasty jigs that may be utilized in a UKA procedure, reference is made to FIG. 19, which is a flow chart illustrating the methods. As shown in FIG. 19, the target bones are scanned and the resulting images are segmented [blocks 702 and 704]. The resulting segmented images are used to form 3D models of the target bones. The 3D models of the target bones are employed for the surgical planning of the jigs, wherein 3D models of the jigs are positioned on 3D models of the target bones, such positioning being employed to determine cavity generation for the jigs that will allow the actual resulting jigs to matingly receive the actual corresponding surfaces of the actual target bones [blocks 706 and 708]. The information determined from the surgical planning is used to CNC machine or otherwise manufacture (e.g., SLA or other rapid prototyping manufacturing processes) the femoral and tibial jigs [block 710]. Once the femoral and tibial jigs are created, the jigs 2a, 2b are sent to the surgeon for review [block 712]. The jigs are sterilized before use [block 714]. The surgeon prepares the site for the arthroplasty procedure (i.e. makes an incision, etc.), The surgeon fits the femoral jig 2a onto the femur such that the femoral jig 2a matingly receives the corresponding surfaces of the target bone, the jig 2a then being secured to and stabilized on the target bone via pins drilled through the jig 2a and into the target bone [block 716]. The surgeon makes guided cuts in the femur via the guide surfaces in the femoral jig 2a [block 718]. The surgeon then fits the tibial jig 2b onto the tibia such that the tibial jig 2b matingly receives the corresponding surfaces of the target bone, the jig 2b then being secured to and stabilized on the target bone via pins drilled through the jig 2b and into the target bone [block 720]. The surgeon makes guided cuts into the tibia via the guide surfaces in the tibia jig 2b [block 722]. After the cuts are made, the jigs 2a, 2b may be discarded and the implantation of the femur and tibia implants can take place [block 724].

Depending on the type of arthroplasty jig desired, the systems and methods disclosed herein may be applied to both the production of natural alignment arthroplasty jigs, zero degree mechanical axis alignment jigs, or arthroplasty jigs configured to provide a result that is somewhere between natural alignment and zero degree mechanical axis alignment.

Although the present invention has been described with reference to preferred embodiments, persons skilled in the art will recognize that changes may be made in form and detail without departing from the spirit and scope of the invention.

What is claimed is:

1. A tibial arthroplasty jig for assisting in the performance of a tibial arthroplasty procedure on an arthroplasty target region of a tibia of a patient's knee joint, the tibia including a medial articular plateau surface, an intercondyloid eminence surface having a medial upslope, a generally planar area of an anterior side of a tibial shaft, a tibial plateau edge, a tibial tuberosity, and a region extending from anterior the intercondyloid eminence to towards the tuberosity over an edge transition from a tibial plateau region, the tibial arthroplasty procedure being associated with an implantation of a prosthetic tibial implant, the jig comprising:
a mating surface including a customized surface contour that is generally a negative of the medial articular plateau surface, the intercondyloid eminence surface, and the generally planar area of the anterior side of the tibial shaft,
wherein the mating surface is configured to make contact with the tibia that includes, and is limited to, contact with the medial articular plateau surface, the intercondyloid eminence surface, and the generally planar area of the anterior side of the tibial shaft when the jig is applied to the tibia to perform the tibial arthroplasty procedure on the arthroplasty target region.

2. The tibial arthroplasty jig of claim 1, further comprising a cutting guide surface positioned and oriented relative to the mating surface to result in a cut in the arthroplasty target region with a desired position and orientation.

3. The tibial arthroplasty jig of claim 2, wherein the desired position and orientation allows the prosthetic tibial implant to restore the patient's knee joint to a natural alignment.

4. The femoral arthroplasty jig of claim 2, further comprising a jig body of unitary construction and wherein the cutting guide surface and the mating surface are defined in the jig body.

5. The tibial arthroplasty jig of claim 1, wherein the contact with the generally planar area of the anterior side of the tibial shaft is limited to being generally distal of the tibial plateau edge and generally proximal of the tibial tuberosity.

6. The tibial arthroplasty jig of claim 1, wherein the contact with the intercondyloid eminence is limited to the medial upslope of the intercondyloid eminence.

7. The tibial arthroplasty jig of claim 1, wherein the contact with the intercondyloid eminence is generally limited to the medial upslope of the intercondyloid eminence and the region extending from anterior the intercondyloid eminence to towards the tuberosity over the edge transition from the tibial plateau region.

8. The tibial arthroplasty jig of claim 7, wherein the contact with the intercondyloid eminence merges with contact associated with the generally planar area of the anterior side of the tibial shaft.

9. The tibial arthroplasty jig of claim 1, wherein the jig is a unicompartmental tibial arthroplasty jig configured for assisting in the performance of a unicompartmental tibial arthroplasty procedure.

10. A tibial arthroplasty jig for assisting in the performance of a tibial arthroplasty procedure on an arthroplasty target region of a tibia of a patient's knee joint, the tibia including a generally planar area of an anterior side of a tibial shaft distal of a tibial plateau edge and generally proximal of a tibial tuberosity, the tibia further including a medial tibia condyle, the tibial tuberosity including a medial edge, a lateral edge, a proximal boundary and a beginning of a distal half to distal third of the tibial tuberosity the tibial arthroplasty procedure being associated with an implantation of a prosthetic tibial implant, the jig comprising:
a mating surface including a customized surface contour that is generally a negative of the generally planar area of the anterior side of the tibial shaft distal of the tibial plateau edge and generally proximal of the tibial tuberosity,
wherein the mating surface is configured to make tibia contact that includes contact with the generally planar area of the anterior side of the tibial shaft distal of the tibial plateau edge and generally proximal of the tibial tuberosity when the jig is applied to the tibia to perform the tibial arthroplasty procedure on the arthroplasty target region.

11. The tibial arthroplasty jig of claim 10, wherein the contact with the generally planar area extends distally from generally the tibial plateau edge to generally even with the beginning of the distal half to distal third of the tibial tuberosity.

12. The tibial arthroplasty jig of claim 11, wherein the contact with the generally planar area extends medial-lateral from the medial edge of the medial tibia condyle to generally even with the medial edge of the tibial tuberosity.

13. The tibial arthroplasty jig of claim 10, wherein the contact with the generally planar area extends distally from generally the tibial plateau edge to near the proximal boundary of the tibial tuberosity.

14. The tibial arthroplasty jig of claim 13, wherein the contact with the generally planar area extends medial-lateral generally between the lateral edge and the medial edge of the tibial tuberosity.

15. The tibial arthroplasty jig of claim 10, further comprising a cutting guide surface positioned and oriented relative to the mating surface to result in a cut in the arthroplasty target region with a desired position and orientation.

16. The tibial arthroplasty jig of claim 15, wherein the desired position and orientation allows the prosthetic tibial implant to restore the patient's knee joint to a natural alignment.

17. The tibial arthroplasty jig of claim 15, further comprising a jig body of unitary construction and wherein the cutting guide surface and the mating surface are defined in the jig body.

18. The tibial arthroplasty jig of claim 10, wherein the jig is a unicompartmental tibial arthroplasty jig configured for assisting in the performance of a unicompartmental tibial arthroplasty procedure.

* * * * *